(12) United States Patent
Williams

(10) Patent No.: US 9,045,759 B2
(45) Date of Patent: Jun. 2, 2015

(54) DNA PLASMIDS WITH IMPROVED COPY NUMBER

(76) Inventor: James Arthur Williams, Lincoln, NE (US)

( * ) Notice: Subject to any disclaimer, the term of this patent is extended or adjusted under 35 U.S.C. 154(b) by 372 days.

(21) Appl. No.: 12/656,115

(22) Filed: Jan. 19, 2010

(65) Prior Publication Data

US 2010/0184158 A1  Jul. 22, 2010

Related U.S. Application Data

(60) Provisional application No. 61/205,561, filed on Jan. 21, 2009.

(51) Int. Cl.
  *C12N 15/00* (2006.01)
  *C12N 15/69* (2006.01)
  *C12N 15/70* (2006.01)
  *C12N 1/20* (2006.01)

(52) U.S. Cl.
  CPC ............... *C12N 15/69* (2013.01); *C12N 15/70* (2013.01)

(58) Field of Classification Search
  None
  See application file for complete search history.

(56) References Cited

U.S. PATENT DOCUMENTS

| 7,449,335 | B2 * | 11/2008 | Weeks et al. | 435/469 |
| 7,932,029 | B1 * | 4/2011 | Lok | 435/6.12 |
| 2003/0180949 | A1 | 9/2003 | Levy | |

FOREIGN PATENT DOCUMENTS

| WO | WO 2006/023546 | 3/2006 |
| WO | WO 2006/078979 | 7/2006 |
| WO | WO 2008/136790 | 11/2008 |
| WO | WO 2008/153733 | 12/2008 |

OTHER PUBLICATIONS

Watson et al., Gene 70(2):399-408, 1988.*
Carnes, Aaron E. "Fermentation Design for the Manufacture of Therapeutic Plasmid DNA." *BioProcess International*. Oct. 2005. pp. 2-7.
Marians, Kenneth J., et al. "Maximal Limits of the *Escherichia coli* Replication Factor Y Effector Site Sequences in pBR3222 DNA." *The Journal of Biological Chemistry*. vol. 257, No. 10. May 25, 1982. pp. 5256-5662.
Masai, Hisao and Ken-Ichi Arai. "*Escherichia coli dnaT* Gene Function Is Required for pBR322 Plasmid Replication But Not for R1 Plasmid Replication." *Journal of Bacteriology*. vol. 171, No. 6. Jun. 1989. pp. 2975-2980.
"Cloning vector pBR322, complete sequence." http://www.ncbi.nlm.nih.gov/nuccore/J01749, Sep. 30, 2008.

* cited by examiner

*Primary Examiner* — Nancy T Vogel

(57) ABSTRACT

The present invention relates to the production of covalently closed circular (ccc) recombinant DNA molecules such as plasmids, cosmids, bacterial artificial chromosomes (BACs), bacteriophages, viral vectors and hybrids thereof, and more particularly to vector modifications that improve production yield of said DNA molecules in fermentation culture.

2 Claims, 3 Drawing Sheets

FIGURE 1: pBR322 origin schematic

text continues …

SEQUENCE LISTING

<160> NUMBER OF SEQ ID NOS: 14

<210> SEQ ID NO 1
<211> LENGTH: 6826
<212> TYPE: DNA
<213> ORGANISM: Artificial Sequence
<220> FEATURE:
<223> OTHER INFORMATION: Description of Artificial Sequence: pNTCUltra1 PAS-BH

<400> SEQUENCE: 1

```
cgggcttttt tttcttaggc tgcctcgcgc gtttcggtga tgacggtgaa aacctctgac      60
acatgcagct cccggagacg gtcacagctt gtctgtaagc ggatgccggg agcagacaag     120
cccgtcaggg cgcgtcagcg ggtgttggcg ggtgtcgggg cgcagccatg acccagtcac     180
gtagcgatag cggagtgtat actggcttaa ctatgcggca tcagagcaga ttgtactgag     240
agtgcaccat atgcggtgtg aaataccgca cagatgcgta aggagaaaat accgcatcag     300
gcgctcttcc gcttcctcgc tcactgactc gctgcgctcg tcgttcggc tgcggcgagc      360 ggtatcagct cactcaaagg cggtaatacg ttatccaca gaatcagggg ataacgcagg      420
aaagaacatg tgagcaaaag gccagcaaaa ggccaggaac cgtaaaaagg ccgcgttgct     480 ggcgttttc cataggctcc gccccctga cgagcatcac aaaaatcgac gctcaagtca      540
gaggtggcga aacccgacag gactataaag ataccaggcg tttccccctg gaagctccct     600
cgtgcgctct cctgttccga ccctgccgct taccggatac ctgtccgcct ttctcccttc     660
gggaagcgtg gcgctttctc atagctcacg ctgtaggtat ctcagttcgg tgtaggtcgt     720
tcgctccaag ctgggctgtg tgcacgaacc ccccgttcag cccgaccgct gcgccttatc     780
cggtaactat cgtcttgagt ccaacccggt aagacacgac ttatcgccac tggcagcagc     840
cactggtaac aggattagca gagcgaggta tgtaggcggt gctacagagt tcttgaagta     900 gtggcctac tacggctaca ctagaagaac agtatttggt atctgcgctc tgctgaagcc      960
agttaccttc ggaaaaagag ttggtagctc ttgatccggc aaacaaacca ccgctggtag    1020
cggtggtttt tttgtttgca agcagcagat tacgcgcaga aaaaaggat ctcaagaaga     1080 tcctttgatc ttttctacgg gtctgacgc tcagtggaac gaaaactcac gttaagggat     1140
tttggtcatg agattatcaa aaaggatctt cacctagatc cttttaaatt aaaaatgaag    1200
ttttaaatca atctaaagta tatatgagta aacttggtct gacagttacc aatgcttaat    1260
cagtgaggca cctatctcag cgatctgtct atttcgttca tccatagttg cctgactcct    1320
gcaaaccacg ttgtgtctca aaatctctga tgttacattg cacaagataa aaatatatca    1380
tcatgaacaa taaaactgtc tgcttacata acagtaata caaggggtgt tatgagccat     1440
attcaacggg aaacgtcttg ctcgaggccg cgattaaatt ccaacatgga tgctgattta    1500
```

```
tatgggtata aatgggctcg cgataatgtc gggcaatcag gtgcgacaat ctatcgattg    1560
tatgggaagc ccgatgcgcc agagttgttt ctgaaacatg gcaaaggtag cgttgccaat    1620
gatgttacag atgagatggt cagactaaac tggctgacgg aatttatgcc tcttccgacc    1680
atcaagcatt ttatccgtac tcctgatgat gcatggttac tcaccactgc gatccccggg    1740
aaaacagcat tccaggtatt agaagaatat cctgattcag gtgaaaatat tgttgatgcg    1800
ctggcagtgt tcctgcgccg gttgcattcg attcctgttt gtaattgtcc ttttaacagc    1860
gatcgcgtat ttcgtctcgc tcaggcgcaa tcacgaatga ataacggttt ggttgatgcg    1920
agtgattttg atgacgagcg taatggctgg cctgttgaac aagtctggaa agaaatgcat    1980
aagcttttgc cattctcacc ggattcagtc gtcactcatg gtgatttctc acttgataac    2040 cttattttg acgaggggaa attaataggt tgtattgatg ttggacgagt cggaatcgca    2100
gaccgatacc aggatcttgc catcctatgg aactgcctcg gtgagttttc tccttcatta    2160
cagaaacggc tttttcaaaa atatggtatt gataatcctg atatgaataa attgcagttt    2220
catttgatgc tcgatgagtt tttctaagcc ctgatcactg tggaatgtgt gtcagttagg    2280
gtgtggaaag tccccaggct ccccagcagg cagaagtatg caaagcatgc atctcaatta    2340
gtcagcaacc aggtgtggaa agtccccagg ctccccagca ggcagaagta tgcaaagcat    2400
gcatctcaat tagtcagcaa ccatagtccc gcccctaact ccgccatcc cgcccctaac    2460 tccgcccagg atccgctcta gatggccatt gcatacgttg tatccatatc ataatatgta    2520
catttatatt ggctcatgtc caacattacc gccatgttga cattgattat tgactagtta    2580
ttaatagtaa tcaattacgg ggtcattagt tcatagccca tatatggagt tccgcgttac    2640
ataacttacg gtaaatggcc cgcctggctg accgcccaac gacccccgcc cattgacgtc    2700
aataatgacg tatgttccca tagtaacgcc aatagggact ttccattgac gtcaatgggt    2760
ggagtattta cggtaaactg cccacttggc agtacatcaa gtgtatcata tgccaagtac    2820
gccccctatt gacgtcaatg acggtaaatg gcccgcctgg cattatgccc agtacatgac    2880
cttatgggac tttcctactt ggcagtacat ctacgtatta gtcatcgcta ttaccatggt    2940
gatgcggttt tggcagtaca tcaatgggcg tggatagcgg tttgactcac ggggatttcc    3000
aagtctccac cccattgacg tcaatgggag tttgttttgg caccaaaatc aacgggactt    3060
tccaaaatgt cgtaacaact ccgccccatt gacgcaaatg ggcggtaggc gtgtacggtg    3120
ggaggtctat ataagcagag ctcgtttagt gaaccgtcag acacttgcta agacaataa    3180 caaatttact tgcaatcccc caaaacagac aggtaagtat ccttttttaca gcacaactta    3240 atgagacaga tagaaactgg tcttgtagaa acagagtagt cgcctgcttt tctgccaggt    3300
gctgacttct ctcccctggg cttttttctt tttctcaggt tgaaaagaag aagacgaaga    3360
agacgaagaa gacaaagccg ccaccatgca gatcttcgtg aagaccctga cgggcaagac    3420
caccactctt ggggtcgagc ccagtgacac catcgagaat gtcaaggcca agatccaaga    3480
caaggaaggc atcccacctg accagcagag gctgatattc gcgggcaaac agctggagga    3540
tggccgcacc ctgtccgact acaacatcca gaaagagtcc accttgcacc tggtgctgcg    3600
tctgcgcggt gccgctatgg aggtgaagca ggagaaccgg ctgctcaacg aaagcgaaag    3660
cagcagccag ggcctgctcg gctactactt cagcgacctg aacttccagg ctcccatggt    3720
ggtgaccagc agcaccaccg cgatctgag catcccagc agcagctgg agaacatccc    3780 cagcgagaac cagtacttcc agagcgccat ctggagcggc ttcatcaagg tgaagaaaag    3840
```

-continued

```
cgatgagtac accttcgcta ccagcgctga caaccacgtg accatgtggg tggacgatca      3900
ggaagtgatc aacaaggcca gcaacagcaa caaaatccgg ctggagaagg gccggctgta      3960
ccagatcaag atccagtacc agcgggaaaa ccccaccgag aagggcctgg acttcaagct      4020
gtactggacc gacagccaga acaagaaaga agtgatcagc agcgataacc tgcagctgcc      4080
cgagctgaag cagaagagca gcaacagccg gaaaaaacgg agcaccagcg ctggccccac      4140
cgtgcccgat cgggataacg atggcatccc cgatagcctg gaagtggagg gctacaccgt      4200
ggacgtgaag aacaaacgga ccttcctgag cccctggatc agcaacatcc acgagaagaa      4260
aggcctgacc aagtacaaaa gcagcccgga aaatggagc accgctagcg accctacag      4320
cgatttcgag aaggtgaccg gccggatcga caaaaacgtg agccccgaag ctcggcaccc      4380
cctggtggct gcttacccca tcgtgcacgt ggacatggag aacatcatcc tgagcaagaa      4440
cgaagatcag agcaccccaga acaccgacag cgagacccgg accatcagca aaaacaccag      4500
caccagccgg acccacacca gcgaagtgca cggcaacgcc gaggtgcacg ctagcttctt      4560
cgatatcggc ggcagcgtga cgctggctt cagcaacagc aacagcagca cgtggctat      4620
cgatcacagc ctgagcctgg ctggcgaacg gacctgggct gaaaccatgg gcctgaacac      4680
cgctgatacc gctcggctga acgctaacat ccggtacgtg aacaccggca ccgctcccat      4740
ctacaacgtg ctgcccacca ccagcctggt gctgggcaag aaccagaccc tggccaccat      4800
caaggccaag gaaaaccagc tgagccagat cctggccccc aacaactact accccagcaa      4860
aaacctggct cccatcgctc tgaacgctca ggacgattc agcagcaccc ccatcaccat      4920
gaactacaac cagttcctgg agctggagaa gaccaaacag ctgcggctgg ataccgacca      4980
ggtgtacggc aacatcgcca cctacaactt cgaaaacggc cggttgcggg tggataccgg      5040
cagcaactgg agcgaagtgc tgccccagat ccaggaaacc accgcccgga tcatcttcaa      5100
cggcaaggat ctgaacctgg tggaacggcg gatcgctgct gtgaacccca gcgatcccct      5160
ggagaccacc aaacccgaca tgaccctgaa ggaggccctg aagatcgcct tcggcttcaa      5220
cgaacccaac ggcaacctgc agtaccaggg caaggacatc accgagttcg acttcaactt      5280
cgaccagcag accagccaga acatcaaaaa ccagctggcc gagctgaacg ccaccaacat      5340
ctacaccgtg ctggacaaga tcaagctgaa cgccaagatg aacatcctga tccgggacaa      5400
gcggttccac tacgatcgga caacatcgc tgtgggcgct gatgaaagcg tggtgaagga      5460
agctcaccgg gaagtgatca acagcagcac cgagggcctg ctcctgaaca tcgacaagga      5520
catccggaag atcctgagcg gctacatcgt ggagatcgag gacaccgagg gcctgaagga      5580
agtgatcaac gaccggtacg acatgctgaa catcagcagc ctgcggcagg acggcaagac      5640
cttcatcgac ttcaagaaat acaacgacaa gctgccctg tacatcagca cccccaacta      5700
caaggtgaac gtgtacgccg tgaccaagga gaacaccatc atcaacccca gcgaaaacgg      5760
cgacaccagc accaacggca tcaagaaaat cctgatcttc agcaagaaag gctacgagat      5820
cggcggcccg gtcgccacca tggtgagcaa gggcgaggag ctgttcaccg ggtggtgcc      5880
catcctggtc gagctggacg gcgacgtaaa cggccacaag ttcagcgtgt ccggcgaggg      5940
cgagggcgat gccacctacg gcaagctgac cctgaagttc atctgcacca ccggcaagct      6000
gcccgtgccc tggcccaccc tcgtgaccac cctgacctac ggcgtgcagt gcttcagccg      6060
ctaccccgac cacatgaagc agcacgactt cttcaagtcc gccatgcccg aaggctacgt      6120
ccaggagcgc accatcttct tcaaggacga cggcaactac aagacccgcg ccgaggtgaa      6180
gttcgagggc gacaccctgg tgaaccgcat cgagctgaag ggcatcgact tcaaggagga      6240
```

```
cggcaacatc ctggggcaca agctggagta caactacaac agccacaacg tctatatcat    6300
ggccgacaag cagaagaacg gcatcaaggt gaacttcaag atccgccaca acatcgagga    6360
cggcagcgtg cagctcgccg accactacca gcagaacacc cccatcggcg acggcccccgt   6420 gctgctgccc gacaaccact acctgagcac ccagtccgcc ctgagcaaag accccaacga    6480
gaagcgcgat cacatggtcc tgctggagtt cgtgaccgcc gccgggatca ctctcggcat    6540
ggacgagctg tacaagtaac tcgagccgca gatctttttc cctctgccaa aaattatggg    6600
gacatcatga agccccttga gcatctgact tctggctaat aaaggaaatt tattttcattg   6660 caatagtgtg ttggaatttt ttgtgtctct cactcggaag gacataaggg cggccgcaac    6720
gacgagaacg aacgaagaac gctcgagagt cgatttaaat ccccccctgta tcgatgcact   6780 gcctcgatgc tgcatcgatg cacaaaatgc tagcccgcct aatgag                   6826

<210> SEQ ID NO 2
<211> LENGTH: 212
<212> TYPE: DNA
<213> ORGANISM: Artificial Sequence
<220> FEATURE:
<223> OTHER INFORMATION: Description of Artificial Sequence: SV40
      enhancer

<400> SEQUENCE: 2
ctgtggaatg tgtgtcagtt agggtgtgga agtccccag gctccccagc aggcagaagt      60
atgcaaagca tgcatctcaa ttagtcagca accaggtgtg gaaagtcccc aggctcccca   120
gcaggcagaa gtatgcaaag catgcatctc aattagtcag caaccatagt cccgccccta   180
actccgccca tcccgcccct aactccgccc ag                                 212

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: PAS-BH

<400> SEQUENCE: 3
cagctcccgg agacggtcac agcttgtctg taagcggatg ccgggagc                 48

<210> SEQ ID NO 4
<211> LENGTH: 285
<212> TYPE: DNA
<213> ORGANISM: Artificial Sequence
<220> FEATURE:
<223> OTHER INFORMATION: Description of Artificial Sequence: pBR322
      origin region between ROP and  PAS-BL  (pBR322 2067-2351)

<400> SEQUENCE: 4
ctgcctcgcg cgtttcggtg atgacggtga aaacctctga cacatgcagc tcccggagac     60
ggtcacagct tgtctgtaag cggatgccgg gagcagacaa gcccgtcagg gcgcgtcagc   120
gggtgttggc gggtgtcggg gcgcagccat gacccagtca cgtagcgata gcggagtgta   180
tactggctta actatgcggc atcagagcag attgtactga gagtgcacca tatgcggtgt   240
gaaataccgc acagatgcgt aaggagaaaa taccgcatca ggcgc                   285

<210> SEQ ID NO 5
<211> LENGTH: 101
<212> TYPE: DNA
<213> ORGANISM: Artificial Sequence
<220> FEATURE:
```

<223> OTHER INFORMATION: Description of Artificial Sequence: ApaI-KpnI
      dual terminator

<400> SEQUENCE: 5

| | | | | | |
|---|---|---|---|---|---|
| gggcccaccg | atacaattaa | aggctccttt | tggagccttt | ttttttggac | tgcaaacaaa | 60 |
| tagtcaaaag | cctccggtcg | gaggcttttg | actttggtac | c | | 101 |

<210> SEQ ID NO 6
<211> LENGTH: 3095
<212> TYPE: DNA
<213> ORGANISM: Artificial Sequence
<220> FEATURE:
<223> OTHER INFORMATION: Description of Artificial Sequence: NTC8685

<400> SEQUENCE: 6

| | | | | | |
|---|---|---|---|---|---|
| ccgcctaatg | agcgggcttt | ttttcttag | ggtgcaaaag | gagagcctgt | aagcgggcac | 60 |
| tcttccgtgg | tctggtggat | aaattcgcaa | gggtatcatg | gcggacgacc | ggggttcgag | 120 |
| ccccgtatcc | ggccgtccgc | cgtgatccat | gcggttaccg | cccgcgtgtc | gaacccaggt | 180 |
| gtgcgacgtc | agacaacggg | ggagtgctcc | ttttggcttc | cttcccctac | cggtctgcct | 240 |
| cgcgcgtttc | ggtgatgacg | gtgaaaacct | ctgacacatg | cagctcccgg | agacggtcac | 300 |
| agcttgtctg | taagcggatg | ccgggagcag | acaagcccgt | cagggcgcgt | cagcgggtgt | 360 |
| tggcgggtgt | cggggcgcag | ccatgaccca | gtcacgtagc | gatagcggag | tgtatactgg | 420 |
| cttaactatg | cggcatcaga | gcagattgta | ctgagagtgc | accatatgcg | gtgtgaaata | 480 |
| ccgcacagat | gcgtaaggag | aaaataccgc | atcaggcgct | cttccgcttc | ctcgctcact | 540 |
| gactcgctgc | gctcggtcgt | tcggctgcgg | cgagcggtat | cagctcactc | aaaggcggta | 600 |
| atacggttat | ccacagaatc | aggggataac | gcaggaaaga | acatgtgagc | aaaaggccag | 660 |
| caaaaggcca | ggaaccgtaa | aaaggccgcg | ttgctggcgt | ttttccatag | gctccgcccc | 720 |
| cctgacgagc | atcacaaaaa | tcgacgctca | agtcagaggt | ggcgaaaccc | gacaggacta | 780 |
| taaagatacc | aggcgtttcc | ccctggaagc | tccctcgtgc | gctctcctgt | tccgaccctg | 840 |
| ccgcttaccg | gatacctgtc | cgcctttctc | ccttcgggaa | gcgtggcgct | ttctcatagc | 900 |
| tcacgctgta | ggtatctcag | ttcggtgtag | gtcgttcgct | ccaagctggg | ctgtgtgcac | 960 |
| gaaccccccg | ttcagcccga | ccgctgcgcc | ttatccggta | actatcgtct | tgagtccaac | 1020 |
| ccggtaagac | acgacttatc | gccactggca | gcagccactg | gtaacaggat | tagcagagcg | 1080 |
| aggtatgtag | gcggtgctac | agagttcttg | aagtggtggc | ctaactacgg | ctacactaga | 1140 |
| agaacagtat | ttggtatctg | cgctctgctg | aagccagtta | ccttcggaaa | aagagttggt | 1200 |
| agctcttgat | ccggcaaaca | aaccaccgct | ggtagcggtg | gtttttttgt | ttgcaagcag | 1260 |
| cagattacgc | gcagaaaaaa | aggatctcaa | gaagatcctt | tgatcttttc | tacgggtct | 1320 |
| gacgctcagt | ggaacgaaaa | ctcacgttaa | gggattttgg | tcatgagatt | atcaaaaagg | 1380 |
| atcttcacct | agatcctttt | aaattaaaaa | tgaagtttta | aatcaatcta | agtatatat | 1440 |
| gagtaaactt | ggtctgacag | ttaccaatgc | ttaatcagtg | aggcacctat | ctcagcgatc | 1500 |
| tgtctatttc | gttcatccat | agttgcctga | ctcctgcaaa | ccacgttgtg | gtagaattgg | 1560 |
| taaagagagt | cgtgtaaaat | atcgagttcg | cacatcttgt | tgtctgatta | ttgatttttg | 1620 |
| gcgaaaccat | ttgatcatat | gacaagatgt | gtatctacct | taacttaatg | attttgataa | 1680 |
| aaatcattag | gtacccctga | tcactgtgga | atgtgtgtca | gttagggtgt | ggaaagtccc | 1740 |
| caggctcccc | agcaggcaga | agtatgcaaa | gcatgcatct | caattagtca | gcaaccaggt | 1800 |

```
gtggaaagtc cccaggctcc ccagcaggca gaagtatgca aagcatgcat ctcaattagt    1860
cagcaaccat agtcccgccc ctaactccgc ccatcccgcc cctaactccg cccagttacg    1920
gggtcattag ttcatagccc atatatggag ttccgcgtta cataacttac ggtaaatggc    1980
ccgcctggct gaccgccaaa cgaccccgc ccattgacgt caataatgac gtatgttccc    2040
atagtaacgc caatagggac tttccattga cgtcaatggg tggagtattt acggtaaact    2100
gcccacttgg cagtacatca agtgtatcat atgccaagta cgccccctat tgacgtcaat    2160
gacggtaaat ggcccgcctg gcattatgcc cagtacatga ccttatggga ctttcctact    2220
tggcagtaca tctacgtatt agtcatcgct attaccatgg tgatgcggtt ttggcagtac    2280
atcaatgggc gtggatagcg gtttgactca cggggatttc caagtctcca ccccattgac    2340
gtcaatggga gtttgttttg gcaccaaaat caacgggact ttccaaaatg tcgtaacaac    2400
tccgccccat tgacgcaaat gggcggtagg cgtgtacggt gggaggtcta taagcaga    2460
gctcgtttag tgaaccgtca gatcgcctgg agacgccatc cacgctgttt tgacctccat    2520
agaagacacc gggaccgatc cagcctccgc ggctcgcatc tctccttcac gcgcccgccg    2580
ccctacctga gccgccatc cacgccggtt gagtcgcgtt ctgccgcctc ccgcctgtgg    2640
tgcctcctga actgcgtccg ccgtctaggt aagtttaaag ctcaggtcga gacgggcct    2700
ttgtccggcg ctcccttgga gcctacctag actcagccgg ctctccacgc tttgcctgac    2760
cctgcttgct caactctagt tctctcgtta acttaatgag acagatagaa actggtcttg    2820
tagaaacaga gtagtcgcct gcttttctgc caggtgctga cttctctccc ctgggctttt    2880
ttcttttct caggttgaaa agaagaagac gaagaagacg aagaagacaa accgtcgtcg    2940
acagatcttt ttccctctgc caaaaattat ggggacatca tgaagcccct tgagcatctg    3000
acttctggct aataaaggaa atttatttc attgcaaatag tgtgttggaa ttttttgtgt    3060
ctctcactcg gaaggacata agggcggccg ctagc                              3095
```

<210> SEQ ID NO 7
<211> LENGTH: 3016
<212> TYPE: DNA
<213> ORGANISM: Artificial Sequence
<220> FEATURE:
<223> OTHER INFORMATION: Description of Artificial Sequence: NTC8485

<400> SEQUENCE: 7

```
ccgcctaatg agcgggcttt ttttttcttag gctgcctcgc gcgtttcggt gatgacggtg      60
aaaacctctg acacatgcag ctcccggaga cggtcacagc ttgtctgtaa gcggatgccg     120
ggagcagaca agcccgtcag gcgcgtcag cgggtgttgg cgggtgtcgg ggcgcagcca     180
tgacccagtc acgtagcgat agcggagtgt atactggctt aactatgcgg catcagagca     240
gattgtactg agagtgcacc atatgcggtg tgaaataccg cacagatgcg taaggagaaa     300
ataccgcatc aggcgctctt ccgcttcctc gctcactgac tcgctgcgct cggtcgttcg     360
gctgcggcga gcggtatcag ctcactcaaa ggcggtaata cggttatcca cagaatcagg     420
ggataacgca ggaaagaaca tgtgagcaaa aggccagcaa aaggccagga accgtaaaaa     480
ggccgcgttg ctggcgtttt tccataggct ccgcccccct gacgagcatc acaaaaatcg     540
acgctcaagt cagaggtggc gaaacccgac aggactataa agataccagg cgtttccccc     600
tggaagctcc ctcgtgcgct ctcctgttcc gaccctgccg cttaccggat acctgtccgc     660
ctttctccct tcgggaagcg tggcgctttc tcatagctca cgctgtaggt atctcagttc     720
ggtgtaggtc gttcgctcca agctgggctg tgtgcacgaa ccccccgttc agcccgaccg     780
```

```
ctgcgcctta tccggtaact atcgtcttga gtccaacccg gtaagacacg acttatcgcc    840
actggcagca gccactggta acaggattag cagagcgagg tatgtaggcg gtgctacaga    900
gttcttgaag tggtggccta actacggcta cactagaaga acagtatttg gtatctgcgc    960
tctgctgaag ccagttacct tcggaaaaag agttggtagc tcttgatccg gcaaacaaac   1020
caccgctggt agcggtggtt ttttttgtttg caagcagcag attacgcgca gaaaaaagg   1080 atctcaagaa gatcctttga tcttttctac ggggtctgac gctcagtgga acgaaaactc   1140
acgttaaggg attttggtca tgagattatc aaaaggatc ttcacctaga tccttttaaa   1200
ttaaaaatga agttttaaat caatctaaag tatatatgag taaacttggt ctgacagtta   1260
ccaatgctta atcagtgagg cacctatctc agcgatctgt ctatttcgtt catccatagt   1320
tgcctgactc ctgcaaacca cgttgtggta gaattggtaa agagagtcgt gtaaaatatc   1380
gagttcgcac atcttgttgt ctgattattg attttttggcg aaaccatttg atcatatgac   1440
aagatgtgta tctaccttaa cttaatgatt ttgataaaaa tcattaggta cccctgatca   1500
ctgtggaatg tgtgtcagtt agggtgtgga agtccccag gctccccagc aggcagaagt   1560
atgcaaagca tgcatctcaa ttagtcagca accaggtgtg gaaagtcccc aggctcccca   1620
gcaggcagaa gtatgcaaag catgcatctc aattagtcag caaccatagt cccgcccta   1680 actccgccca tcccgcccct aactccgccc aggatccgct ctagatggcc attgcatacg   1740
ttgtatccat atcataatat gtacatttat attggctcat gtccaacatt accgccatgt   1800
tgacattgat tattgactag ttattaatag taatcaatta cggggtcatt agttcatagc   1860
ccatatatgg agttccgcgt tacataactt acggtaaatg gcccgcctgg ctgaccgccc   1920 aacgacccc gcccattgac gtcaataatg acgtatgttc ccatagtaac gccaataggg   1980
actttccatt gacgtcaatg ggtggagtat ttacggtaaa ctgcccactt ggcagtacat   2040
caagtgtatc atatgccaag tacgccccct attgacgtca atgacggtaa atggcccgcc   2100
tggcattatg cccagtacat gaccttatgg gactttccta cttggcagta catctacgta   2160
ttagtcatcg ctattaccat ggtgatgcgg ttttggcagt acatcaatgg gcgtggatag   2220
cggtttgact cacggggatt tccaagtctc cacccattg acgtcaatgg gagtttgttt   2280
tggcaccaaa atcaacggga ctttccaaaa tgtcgtaaca actccgcccc attgacgcaa   2340
atgggcggta ggcgtgtacg gtgggaggtc tatataagca gagctcgttt agtgaaccgt   2400
cagatcgcct ggagacgcca tccacgctgt tttgacctcc atagaagaca ccgggaccga   2460
tccagcctcc gcggctcgca tctctccttc acgcgcccgc cgccctacct gaggccgcca   2520
tccacgccgg ttgagtcgcg ttctgccgcc tcccgcctgt ggtgcctcct gaactgcgtc   2580
cgccgtctag gtaagtttaa agctcaggtc gagaccgggc ctttgtccgg cgctcccttg   2640
gagcctacct agactcagcc ggctctccac gctttgcctg accctgcttg ctcaactcta   2700
gttctctcgt taacttaatg agacagatag aaactggtct tgtagaaaca gagtagtcgc   2760 ctgctttttct gccaggtgct gacttctctc ccctgggctt tttctttttt ctcaggttga   2820
aaagaagaag acgaagaaga cgaagaagac aaaccgtcgt cgacagatct tttccctct   2880 gccaaaaatt atgggacat catgaagccc cttgagcatc tgacttctgg ctaataaagg   2940
aaatttattt tcattgcaat agtgtgttgg aatttttgt gtctctcact cggaaggaca   3000
taaggcggcc gctagc                                                   3016
```

<210> SEQ ID NO 8

<211> LENGTH: 3186
<212> TYPE: DNA
<213> ORGANISM: Artificial Sequence
<220> FEATURE:
<223> OTHER INFORMATION: Description of Artificial Sequence: NTC8682

<400> SEQUENCE: 8

| | | | | | |
|---|---|---|---|---|---|
| ccgcctaatg | agcgggcttt | tttttcttag | ggtgcaaaag | gagagcctgt aagcgggcac | 60 |
| tcttccgtgg | tctggtggat | aaattcgcaa | gggtatcatg | gcggacgacc gggggttcgag | 120 |
| ccccgtatcc | ggccgtccgc | cgtgatccat | gcggttaccg | cccgcgtgtc gaacccaggt | 180 |
| gtgcgacgtc | agacaacggg | ggagtgctcc | ttttggcttc | cttccctac cggtctgcct | 240 |
| cgcgcgtttc | ggtgatgacg | gtgaaaacct | ctgacacatg | cagctcccgg agacggtcac | 300 |
| agcttgtctg | taagcggatg | ccgggagcag | acaagcccgt | cagggcgcgt cagcgggtgt | 360 |
| tggcgggtgt | cggggcgcag | ccatgaccca | gtcacgtagc | gatagcggag tgtatactgg | 420 |
| cttaactatg | cggcatcaga | gcagattgta | ctgagagtgc | accatatgcg gtgtgaaata | 480 |
| ccgcacagat | gcgtaaggag | aaaataccgc | atcaggcgct | cttccgcttc ctcgctcact | 540 |
| gactcgctgc | gctcggtcgt | tcggctgcgg | cgagcggtat | cagctcactc aaaggcggta | 600 |
| atacggttat | ccacagaatc | aggggataac | gcaggaaaga | acatgtgagc aaaaggccag | 660 |
| caaaaggcca | ggaaccgtaa | aaaggccgcg | ttgctggcgt | ttttccatag gctccgcccc | 720 |
| cctgacgagc | atcacaaaaa | tcgacgctca | agtcagaggt | ggcgaaaccc gacaggacta | 780 |
| taaagatacc | aggcgtttcc | ccctggaagc | tccctcgtgc | gctctcctgt tccgaccctg | 840 |
| ccgcttaccg | gatacctgtc | cgcctttctc | ccttcgggaa | gcgtggcgct ttctcatagc | 900 |
| tcacgctgta | ggtatctcag | ttcggtgtag | gtcgttcgct | ccaagctggg ctgtgtgcac | 960 |
| gaaccccccg | ttcagcccga | ccgctgcgcc | ttatccggta | actatcgtct tgagtccaac | 1020 |
| ccggtaagac | acgacttatc | gccactggca | gcagccactg | gtaacaggat tagcagagcg | 1080 |
| aggtatgtag | gcggtgctac | agagttcttg | aagtggtggc | ctaactacgg ctacactaga | 1140 |
| agaacagtat | ttggtatctg | cgctctgctg | aagccagtta | ccttcggaaa aagagttggt | 1200 |
| agctcttgat | ccggcaaaca | aaccaccgct | ggtagcggtg | gtttttttgt ttgcaagcag | 1260 |
| cagattacgc | gcagaaaaaa | aggatctcaa | gaagatcctt | tgatcttttc tacgggtct | 1320 |
| gacgctcagt | ggaacgaaaa | ctcacgttaa | gggattttgg | tcatgagatt atcaaaaagg | 1380 |
| atcttcacct | agatcctttt | aaattaaaaa | tgaagtttta | aatcaatcta agtatatat | 1440 |
| gagtaaactt | ggtctgacag | ttaccaatgc | ttaatcagtg | aggcacctat ctcagcgatc | 1500 |
| tgtctatttc | gttcatccat | agttgcctga | ctccctgcaaa | ccacgttgtg gtagaattgg | 1560 |
| taaagagagt | cgtgtaaaat | atcgagttcg | cacatcttgt | tgtctgatta ttgattttg | 1620 |
| gcgaaaccat | ttgatcatat | gacaagatgt | gtatctacct | taacttaatg attttgataa | 1680 |
| aaatcattag | gtaccctga | tcactgtgga | atgtgtgtca | gttagggtgt ggaaagtccc | 1740 |
| caggctcccc | agcaggcaga | agtatgcaaa | gcatgcatct | caattagtca gcaaccaggt | 1800 |
| gtggaaagtc | cccaggctcc | ccagcaggca | gaagtatgca | aagcatgcat ctcaattagt | 1860 |
| cagcaaccat | agtcccgccc | ctaactccgc | ccatcccgcc | cctaactccg cccagttacg | 1920 |
| gggtcattag | ttcatagccc | atatatggag | ttccgcgtta | cataacttac ggtaaatggc | 1980 |
| ccgcctggct | gaccgcccaa | cgacccccgc | ccattgacgt | caataatgac gtatgttccc | 2040 |
| atagtaacgc | caatagggac | tttccattga | cgtcaatggg | tggagtattt acggtaaact | 2100 |
| gcccacttgg | cagtacatca | agtgtatcat | atgccaagta | cgccccctat tgacgtcaat | 2160 |

```
gacggtaaat ggcccgcctg gcattatgcc cagtacatga ccttatggga ctttcctact    2220
tggcagtaca tctacgtatt agtcatcgct attaccatgg tgatgcggtt ttggcagtac    2280
atcaatgggc gtggatagcg gtttgactca cggggatttc caagtctcca ccccattgac    2340
gtcaatggga gtttgttttg gcaccaaaat caacgggact ttccaaaatg tcgtaacaac    2400
tccgccccat tgacgcaaat gggcggtagg cgtgtacggt gggaggtcta tataagcaga    2460
gctcgtttag tgaaccgtca gatcgcctgg agacgccatc cacgctgttt tgacctccat    2520
agaagacacc gggaccgatc cagcctccgc ggctcgcatc tctccttcac gcgcccgccg    2580
ccctacctga gccgccatc cacgccggtt gagtcgcgtt ctgccgcctc cgcctgtgg    2640 tgcctcctga actgcgtccg ccgtctaggt aagtttaaag ctcaggtcga ccgggcct    2700 ttgtccggcg ctcccttgga gcctacctag actcagccgg ctctccacgc tttgcctgac    2760
cctgcttgct caactctagt tctctcgtta acttaatgag acagatagaa actggtcttg    2820
tagaaacaga gtagtcgcct gcttttctgc caggtgctga cttctctccc ctgggctttt    2880 ttcttttct caggttgaaa agaagaagac gaagaagacg aagaagacaa gccgccacc    2940 atggatgcaa tgaagagagg gctctgctgt gtgctgctgc tgtgtggagc agtcttcgtt    3000
tcgcccagcg gtaccggatc cgtcgacggg gggagatctt tttccctctg ccaaaaatta    3060
tggggacatc atgaagcccc ttgagcatct gacttctggc taataaagga aatttatttt    3120
cattgcaata gtgtgttgga attttttgtg tctctcactc ggaaggacat aagggcggcc    3180
gctagc                                                               3186
```

<210> SEQ ID NO 9
<211> LENGTH: 3107
<212> TYPE: DNA
<213> ORGANISM: Artificial Sequence
<220> FEATURE:
<223> OTHER INFORMATION: Description of Artificial Sequence: NTC8482

<400> SEQUENCE: 9

```
ccgcctaatg agcgggcttt ttttcttag gctgcctcgc gcgtttcggt gatgacggtg     60
aaaacctctg acacatgcag ctcccggaga cggtcacagc ttgtctgtaa gcggatgccg    120
ggagcagaca gcccgtcag ggcgcgtcag cgggtgttgg cgggtgtcgg ggcgcagcca    180
tgacccagtc acgtagcgat agcggagtgt atactggctt aactatgcgg catcagagca    240
gattgtactg agagtgcacc atatgcggtg tgaaataccg cacagatgcg taaggagaaa    300
ataccgcatc aggcgctctt ccgcttcctc gctcactgac tcgctgcgct cggtcgttcg    360
gctgcggcga gcggtatcag ctcactcaaa ggcggtaata cggttatcca cagaatcagg    420
ggataacgca ggaaagaaca tgtgagcaaa aggccagcaa aaggccagga accgtaaaaa    480
ggccgcgttg ctggcgtttt tccataggct ccgcccccct gacgagcatc acaaaaatcg    540
acgctcaagt cagaggtggc gaaacccgac aggactataa agataccagg cgtttccccc    600
tggaagctcc ctcgtgcgct ctcctgttcc gaccctgccg cttaccggat acctgtccgc    660
ctttctccct tcgggaagcg tggcgctttc tcatagctca cgctgtaggt atctcagttc    720
ggtgtaggtc gttcgctcca agctgggctg tgtgcacgaa ccccccgttc agcccgaccg    780
ctgcgcctta tccggtaact atcgtcttga gtccaacccg gtaagacacg acttatcgcc    840
actggcagca gccactggta acaggattag cagagcgagg tatgtaggcg gtgctacaga    900
gttcttgaag tggtggccta actacggcta cactagaaga acagtatttg gtatctgcgc    960
```

```
tctgctgaag ccagttacct tcggaaaaag agttggtagc tcttgatccg gcaaacaaac    1020
caccgctggt agcggtggtt ttttgtttg caagcagcag attacgcgca gaaaaaaagg     1080
atctcaagaa gatcctttga tcttttctac ggggtctgac gctcagtgga acgaaaactc    1140
acgttaaggg attttggtca tgagattatc aaaaaggatc ttcacctaga tccttttaaa    1200
ttaaaaatga agttttaaat caatctaaag tatatatgag taaacttggt ctgacagtta    1260
ccaatgctta atcagtgagg cacctatctc agcgatctgt ctatttcgtt catccatagt    1320
tgcctgactc ctgcaaacca cgttgtggta gaattggtaa agagagtcgt gtaaaatatc    1380
gagttcgcac atcttgttgt ctgattattg attttggcg aaaccatttg atcatatgac     1440
aagatgtgta tctaccttaa cttaatgatt ttgataaaaa tcattaggta ccctgatca     1500
ctgtggaatg tgtgtcagtt agggtgtgga aagtccccag gctccccagc aggcagaagt    1560
atgcaaagca tgcatctcaa ttagtcagca accaggtgtg gaaagtcccc aggctcccca    1620
gcaggcagaa gtatgcaaag catgcatctc aattagtcag caaccatagt cccgccccta    1680
actccgccca tcccgcccct aactccgccc aggatccgct ctagatggcc attgcatacg    1740
ttgtatccat atcataatat gtacatttat attggctcat gtccaacatt accgccatgt    1800
tgacattgat tattgactag ttattaatag taatcaatta cggggtcatt agttcatagc    1860
ccatatatgg agttccgcgt tacataactt acggtaaatg gcccgcctgg ctgaccgccc    1920
aacgacccc gcccattgac gtcaataatg acgtatgttc ccatagtaac gccaataggg     1980
actttccatt gacgtcaatg ggtggagtat ttacggtaaa ctgcccactt ggcagtacat    2040
caagtgtatc atatgccaag tacgccccct attgacgtca atgacggtaa atggcccgcc    2100
tggcattatg cccagtacat gaccttatgg gactttccta cttggcagta catctacgta    2160
ttagtcatcg ctattaccat ggtgatgcgg ttttggcagt acatcaatgg gcgtggatag    2220
cggtttgact cacggggatt tccaagtctc cacccattg acgtcaatgg gagtttgttt     2280
tggcaccaaa atcaacggga ctttccaaaa tgtcgtaaca actccgcccc attgacgcaa    2340
atgggcggta ggcgtgtacg gtgggaggtc tatataagca gagctcgttt agtgaaccgt    2400
cagatcgcct ggagacgcca tccacgctgt tttgacctcc atagaagaca ccgggaccga    2460
tccagcctcc gcggctcgca tctctccttc acgcgcccgc cgccctacct gaggccgcca    2520
tccacgccgg ttgagtcgcg ttctgccgcc tcccgcctgt ggtgcctcct gaactgcgtc    2580
cgccgtctag gtaagtttaa agctcaggtc gagaccgggc ctttgtccgg cgctcccttg    2640
gagcctacct agactcagcc ggctctccac gctttgcctg accctgcttg ctcaactcta    2700
gttctctcgt taacttaatg agacagatag aaactggtct tgtagaaaca gagtagtcgc    2760
ctgcttttct gccaggtgct gacttctctc ccctgggctt ttttctttt ctcaggttga    2820
aaagaagaag acgaagaaga cgaagaagac aaagccgcca ccatggatgc aatgaagaga    2880
gggctctgct gtgtgctgct gctgtgtgga gcagtcttcg tttcgcccag cggtaccgga    2940
tccgtcgacg gggggagatc ttttcctc tgccaaaaat tatggggaca tcatgaagcc      3000
ccttgagcat ctgacttctg gctaataaag gaaatttatt ttcattgcaa tagtgtgttg    3060
gaattttttg tgtctctcac tcggaaggac ataaggcggc cgctagc                 3107
```

<210> SEQ ID NO 10
<211> LENGTH: 3863
<212> TYPE: DNA
<213> ORGANISM: Artificial Sequence
<220> FEATURE:
<223> OTHER INFORMATION: Description of Artificial Sequence: NTC7685

<400> SEQUENCE: 10

```
ccgcctaatg agcgggcttt tttttcttag ggtgcaaaag gagagcctgt aagcgggcac      60
tcttccgtgg tctggtggat aaattcgcaa gggtatcatg gcggacgacc ggggttcgag     120
ccccgtatcc ggccgtccgc cgtgatccat gcggttaccg cccgcgtgtc gaacccaggt     180
gtgcgacgtc agacaacggg ggagtgctcc ttttggcttc cttcccctac cggtctgcct     240
cgcgcgtttc ggtgatgacg gtgaaaacct ctgacacatg cagctcccgg agacggtcac     300
agcttgtctg taagcggatg ccgggagcag acaagcccgt cagggcgcgt cagcgggtgt     360
tggcgggtgt cggggcgcag ccatgaccca gtcacgtagc gatagcggag tgtatactgg     420
cttaactatg cggcatcaga gcagattgta ctgagagtgc accatatgcg gtgtgaaata     480
ccgcacagat gcgtaaggag aaaataccgc atcaggcgct cttccgcttc ctcgctcact     540
gactcgctgc gctcggtcgt tcggctgcgg cgagcggtat cagctcactc aaaggcggta     600
atacggttat ccacagaatc aggggataac gcaggaaaga acatgtgagc aaaaggccag     660
caaaaggcca ggaaccgtaa aaaggccgcg ttgctggcgt ttttccatag gctccgcccc     720
cctgacgagc atcacaaaaa tcgacgctca agtcagaggt ggcgaaaccc gacaggacta     780
taaagatacc aggcgtttcc ccctggaagc tccctcgtgc gctctcctgt tccgaccctg     840
ccgcttaccg gatacctgtc cgcctttctc ccttcgggaa gcgtggcgct ttctcatagc     900
tcacgctgta ggtatctcag ttcggtgtag gtcgttcgct ccaagctggg ctgtgtgcac     960
gaaccccccg ttcagcccga ccgctgcgcc ttatccggta actatcgtct tgagtccaac    1020
ccggtaagac acgacttatc gccactggca gcagccactg gtaacaggat tagcagagcg    1080
aggtatgtag gcggtgctac agagttcttg aagtggtggc ctaactacgg ctacactaga    1140
agaacagtat ttggtatctg cgctctgctg aagccagtta ccttcggaaa aagagttggt    1200
agctcttgat ccggcaaaca aaccaccgct ggtagcggtg ttttttgt ttgcaagcag      1260
cagattacgc gcagaaaaaa aggatctcaa gaagatcctt tgatcttttc tacggggtct    1320
gacgctcagt ggaacgaaaa ctcacgttaa gggattttgg tcatgagatt atcaaaaagg    1380
atcttcacct agatcctttt aaattaaaaa tgaagtttta atcaatcta aagtatatat      1440
gagtaaactt ggtctgacag ttaccaatgc ttaatcagtg aggcacctat ctcagcgatc    1500
tgtctatttc gttcatccat agttgcctga ctccctgcaaa ccacgttgtg tctcaaaatc    1560
tctgatgtta cattgcacaa gataaaaata tatcatcatg aacataaaa ctgtctgctt     1620
acataaacag taatacaagg ggtgttatga gccatattca acgggaaacg tcttgctcga    1680
ggccgcgatt aaattccaac atggatgctg atttatatgg gtataaatgg gctcgcgata    1740
atgtcgggca atcaggtgcg acaatctatc gattgtatgg gaagcccgat gcgccagagt    1800
tgtttctgaa acatggcaaa ggtagcgttg ccaatgatgt tacagatgag atggtcagac    1860
taaactggct gacggaattt atgcctcttc cgaccatcaa gcattttatc cgtactcctg    1920
atgatgcatg gttactcacc actgcgatcc ccgggaaaac agcattccag gtattagaag    1980
aatatcctga ttcaggtgaa aatattgttg atgcgctggc agtgttcctg cgccggttgc    2040
attcgattcc tgtttgtaat gtccttttta acagcgatcg cgtatttcgt ctcgctcagg    2100
cgcaatcacg aatgaataac ggtttggttg atgcgagtga ttttgatgac gagcgtaatg    2160
gctggcctgt tgaacaagtc tggaaagaaa tgcataagct tttgccattc tcaccggatt    2220
cagtcgtcac tcatggtgat ttctcacttg ataaccttat ttttgacgag gggaaattaa    2280
```

```
taggttgtat tgatgttgga cgagtcggaa tcgcagaccg ataccaggat cttgccatcc    2340
tatggaactg cctcggtgag ttttctcctt cattacagaa acggctttt caaaaatatg     2400 gtattgataa tcctgatatg aataaattgc agtttcattt gatgctcgat gagtttttct    2460
aaccctgatc actgtggaat gtgtgtcagt tagggtgtgg aaagtcccca ggctccccag    2520
caggcagaag tatgcaaagc atgcatctca attagtcagc aaccaggtgt ggaaagtccc    2580
caggctcccc agcaggcaga agtatgcaaa gcatgcatct caattagtca gcaaccatag    2640
tcccgcccct aactccgccc atcccgcccc taactccgcc cagttacggg gtcattagtt    2700
catagcccat atatggagtt ccgcgttaca aacttacgg taaatggccc gcctggctga     2760
ccgcccaacg accccgccc attgacgtca ataatgacgt atgttcccat agtaacgcca     2820
atagggactt tccattgacg tcaatgggtg gagtatttac ggtaaactgc ccacttggca    2880
gtacatcaag tgtatcatat gccaagtacg cccctattg acgtcaatga cggtaaatgg     2940
cccgcctggc attatgccca gtacatgacc ttatgggact ttcctacttg gcagtacatc    3000
tacgtattag tcatcgctat taccatggtg atgcggtttt ggcagtacat caatgggcgt    3060
ggatagcggt ttgactcacg gggatttcca agtctccacc ccattgacgt caatgggagt    3120
ttgttttggc accaaaatca acgggacttt ccaaaatgtc gtaacaactc cgccccattg    3180
acgcaaatgg gcggtaggcg tgtacggtgg gaggtctata taagcagagc tcgtttagtg    3240
aaccgtcaga tcgcctggag acgccatcca cgctgttttg acctccatag aagacaccgg    3300
gaccgatcca gcctccgcgg ctcgcatctc tccttcacgc gcccgccgcc ctacctgagg    3360
ccgccatcca cgccggttga gtcgcgttct gccgcctccc gctgtggtg cctcctgaac     3420 tgcgtccgcc gtctaggtaa gtttaaagct caggtcgaga ccgggccttt gtccggcgct    3480
cccttggagc ctacctagac tcagccggct ctccacgctt gcctgaccc tgcttgctca     3540 actctagttc tctcgttaac ttaatgagac agatagaaac tggtcttgta gaaacagagt    3600
agtcgcctgc ttttctgcca ggtgctgact tctctcccct gggctttttt ctttttctca    3660
ggttgaaaag aagaagacga agaagacgaa gaagacaaac cgtcgtcgac agatcttttt    3720
ccctctgcca aaaattatgg ggacatcatg aagccccttg agcatctgac ttctggctaa    3780
taaaggaaat ttatttcat tgcaatagtg tgttggaatt ttttgtgtct ctcactcgga     3840
aggacataag ggcggccgct agc                                            3863
```

<210> SEQ ID NO 11
<211> LENGTH: 3784
<212> TYPE: DNA
<213> ORGANISM: Artificial Sequence
<220> FEATURE:
<223> OTHER INFORMATION: Description of Artificial Sequence: NTC7485

<400> SEQUENCE: 11

```
ccgcctaatg agcgggcttt tttttcttag gctgcctcgc gcgtttcggt gatgacggtg      60
aaaacctctg acacatgcag ctcccggaga cggtcacagc ttgtctgtaa gcggatgccg     120
ggagcagaca agcccgtcag ggcgcgtcag cgggtgttgg cgggtgtcgg ggcgcagcca     180
tgacccagtc acgtagcgat agcggagtgt atactggctt aactatgcgg catcagagca     240
gattgtactg agagtgcacc atatgcggtg tgaaataccg cacagatgcg taaggagaaa     300
ataccgcatc aggcgctctt ccgcttcctc gctcactgac tcgctgcgct cggtcgttcg     360
gctgcggcga gcggtatcag ctcactcaaa ggcggtaata cggttatcca cagaatcagg     420
ggataacgca ggaaagaaca tgtgagcaaa aggccagcaa aaggccagga accgtaaaaa     480
```

```
ggccgcgttg ctggcgtttt tccataggct ccgccccct gacgagcatc acaaaaatcg      540
acgctcaagt cagaggtggc gaaacccgac aggactataa agataccagg cgtttccccc      600
tggaagctcc ctcgtgcgct ctcctgttcc gaccctgccg cttaccggat acctgtccgc      660
ctttctccct tcgggaagcg tggcgctttc tcatagctca cgctgtaggt atctcagttc      720
ggtgtaggtc gttcgctcca agctgggctg tgtgcacgaa ccccccgttc agcccgaccg      780
ctgcgcctta tccggtaact atcgtcttga gtccaacccg gtaagacacg acttatcgcc      840
actggcagca gccactggta acaggattag cagagcgagg tatgtaggcg gtgctacaga      900
gttcttgaag tggtggccta actacggcta cactagaaga acagtatttg gtatctgcgc      960
tctgctgaag ccagttacct tcggaaaaag agttggtagc tcttgatccg gcaaacaaac     1020
caccgctggt agcggtggtt ttttgtttg caagcagcag attacgcgca gaaaaaaagg     1080
atctcaagaa gatcctttga tcttttctac ggggtctgac gctcagtgga acgaaaactc     1140
acgttaaggg attttggtca tgagattatc aaaaaggatc ttcacctaga tccttttaaa     1200
ttaaaaatga agttttaaat caatctaaag tatatatgag taaacttggt ctgacagtta     1260
ccaatgctta atcagtgagg cacctatctc agcgatctgt ctatttcgtt catccatagt     1320
tgcctgactc ctgcaaacca cgttgtgtct caaaatctct gatgttacat tgcacaagat     1380
aaaaatatat catcatgaac aataaaactg tctgcttaca taaacagtaa tacaaggggt     1440
gttatgagcc atattcaacg ggaaacgtct tgctcgaggc cgcgattaaa ttccaacatg     1500
gatgctgatt tatatgggta taaatgggct cgcgataatg tcgggcaatc aggtgcgaca     1560
atctatcgat tgtatgggaa gcccgatgcg ccagagttgt ttctgaaaca tggcaaaggt     1620
agcgttgcca atgatgttac agatgagatg gtcagactaa actggctgac ggaatttatg     1680
cctcttccga ccatcaagca ttttatccgt actcctgatg atgcatggtt actcaccact     1740 gcgatcccg ggaaaacagc attccaggta ttagaagaat atcctgattc aggtgaaaat     1800
attgttgatg cgctggcagt gttcctgcgc cggttgcatt cgattcctgt ttgtaattgt     1860
ccttttaaca gcgatcgcgt atttcgtctc gctcaggcgc aatcacgaat gaataacggt     1920
ttggttgatg cgagtgattt tgatgacgag cgtaatggct ggcctgttga acaagtctgg     1980
aaagaaatgc ataagctttt gccattctca ccggattcag tcgtcactca tggtgatttc     2040
tcacttgata accttatttt tgacgagggg aaattaatag gttgtattga tgttggacga     2100
gtcggaatcg cagaccgata ccaggatctt gccatcctat ggaactgcct cggtgagttt     2160
tctccttcat tacagaaacg ctttttcaa aaatatggta ttgataatcc tgatatgaat     2220
aaattgcagt ttcatttgat gctcgatgag ttttctaac cctgatcact gtggaatgtg     2280
tgtcagttag ggtgtggaaa gtccccaggc tccccagcag gcagaagtat gcaaagcatg     2340
catctcaatt agtcagcaac caggtgtgga agtccccag gctccccagc aggcagaagt     2400
atgcaaagca tgcatctcaa ttagtcagca accatagtcc cgcccctaac tccgcccatc     2460
ccgcccctaa ctccgcccag atccgctct agatggccat tgcatacgtt gtatccatat     2520
cataatatgt acatttatat tggctcatgt ccaacattac cgccatgttg acattgatta     2580
ttgactagtt attaatagta atcaattacg ggtcattag ttcatagccc atatatggag     2640
ttccgcgtta cataacttac ggtaaatggc ccgcctggct gaccgcccaa cgacccccgc     2700
ccattgacgc caataatgac gtatgttccc atagtaacgc caatagggac tttccattga     2760
cgtcaatggg tggagtattt acggtaaact gcccacttgg cagtacatca agtgtatcat     2820
```

```
atgccaagta cgcccctat tgacgtcaat gacggtaaat ggcccgcctg gcattatgcc    2880
cagtacatga ccttatggga ctttcctact tggcagtaca tctacgtatt agtcatcgct    2940
attaccatgg tgatgcggtt ttggcagtac atcaatgggc gtggatagcg gtttgactca    3000
cggggatttc caagtctcca ccccattgac gtcaatggga gtttgttttg gcaccaaaat    3060
caacgggact ttccaaaatg tcgtaacaac tccgccccat tgacgcaaat gggcggtagg    3120
cgtgtacggt gggaggtcta tataagcaga gctcgtttag tgaaccgtca gatcgcctgg    3180
agacgccatc cacgctgttt tgacctccat agaagacacc gggaccgatc cagcctccgc    3240
ggctcgcatc tctccttcac gcgcccgccg ccctacctga gccgccatc cacgccggtt    3300 gagtcgcgtt ctgccgcctc ccgcctgtgg tgcctcctga actgcgtccg ccgtctaggt    3360
aagtttaaag ctcaggtcga gaccgggcct tgtccggcg ctcccttgga gcctacctag    3420
actcagccgg ctctccacgc tttgcctgac cctgcttgct caactctagt tctctcgtta    3480
acttaatgag acagatagaa actggtcttg tagaaacaga gtagtcgcct gcttttctgc    3540
caggtgctga cttctctccc ctgggctttt ttcttttttct caggttgaaa agaagaagac    3600
gaagaagacg aagaagacaa accgtcgtcg acagatcttt tccctctgc caaaaattat    3660 ggggacatca tgaagcccct tgagcatctg acttctggct aataaaggaa atttattttc    3720
attgcaatag tgtgttggaa ttttttgtgt ctctcactcg gaaggacata aggcggccgc    3780
tagc                                                                 3784
```

<210> SEQ ID NO 12
<211> LENGTH: 3954
<212> TYPE: DNA
<213> ORGANISM: Artificial Sequence
<220> FEATURE:
<223> OTHER INFORMATION: Description of Artificial Sequence: NTC7682

<400> SEQUENCE: 12

```
ccgcctaatg agcgggcttt ttttttcttag ggtgcaaaag gagagcctgt aagcgggcac      60
tcttccgtgg tctggtggat aaattcgcaa gggtatcatg gcggacgacc ggggttcgag     120
ccccgtatcc ggccgtccgc cgtgatccat gcggttaccg cccgcgtgtc gaacccaggt     180
gtgcgacgtc agacaacggg ggagtgctcc ttttggcttc cttcccctac cggtctgcct     240
cgcgcgtttc ggtgatgacg gtgaaaacct ctgacacatg cagctcccgg agacggtcac     300
agcttgtctg taagcggatg ccgggagcag acaagcccgt cagggcgcgt cagcgggtgt     360
tggcgggtgt cggggcgcag ccatgaccca gtcacgtagc gatagcggag tgtatactgg     420
cttaactatg cggcatcaga gcagattgta ctgagagtgc accatatgcg gtgtgaaata     480
ccgcacagat gcgtaaggag aaaataccgc atcaggcgct cttccgcttc ctcgctcact     540
gactcgctgc gctcggtcgt tcggctgcgg cgagcggtat cagctcactc aaaggcggta     600
atacggttat ccacagaatc aggggataac gcaggaaaga acatgtgagc aaaaggccag     660
caaaaggcca ggaaccgtaa aaaggccgcg ttgctggcgt ttttccatag gctccgcccc     720
cctgacgagc atcacaaaaa tcgacgctca agtcagaggt ggcgaaaccc gacaggacta     780
taaagatacc aggcgtttcc ccctggaagc tccctcgtgc gctctcctgt tccgaccctg     840
ccgcttaccg gatacctgtc gcctttctcc cttcgggaa gcgtggcgct ttctcatagc     900
tcacgctgta ggtatctcag ttcggtgtag tcgttcgct ccaagctggg ctgtgtgcac     960
gaaccccccg ttcagcccga ccgctgcgcc ttatccggta actatcgtct tgagtccaac    1020
ccggtaagac acgacttatc gccactggca gcagccactg gtaacaggat tagcagagcg    1080
```

```
aggtatgtag gcggtgctac agagttcttg aagtggtggc ctaactacgg ctacactaga    1140
agaacagtat ttggtatctg cgctctgctg aagccagtta ccttcggaaa aagagttggt    1200
agctcttgat ccggcaaaca aaccaccgct ggtagcggtg gtttttttgt ttgcaagcag    1260
cagattacgc gcagaaaaaa aggatctcaa gaagatcctt tgatcttttc tacgggtct     1320
gacgctcagt ggaacgaaaa ctcacgttaa gggattttgg tcatgagatt atcaaaaagg    1380
atcttcacct agatcctttt aaattaaaaa tgaagtttta aatcaatcta agtatatat     1440
gagtaaactt ggtctgacag ttaccaatgc ttaatcagtg aggcacctat ctcagcgatc    1500
tgtctatttc gttcatccat agttgcctga ctccctgcaaa ccacgttgtg tctcaaaatc   1560
tctgatgtta cattgcacaa gataaaaata tatcatcatg aacaataaaa ctgtctgctt    1620
acataaacag taatacaagg ggtgttatga gccatattca acgggaaacg tcttgctcga    1680
ggccgcgatt aaattccaac atggatgctg atttatatgg gtataaatgg ctcgcgata    1740
atgtcgggca atcaggtgcg acaatctatc gattgtatgg gaagcccgat gcgccagagt    1800
tgtttctgaa acatggcaaa ggtagcgttg ccaatgatgt tacagatgag atggtcagac    1860
taaactggct gacggaattt atgcctcttc cgaccatcaa gcattttatc cgtactcctg    1920
atgatgcatg gttactcacc actgcgatcc ccgggaaaac agcattccag gtattagaag    1980
aatatcctga ttcaggtgaa aatattgttg atgcgctggc agtgttcctg cgccggttgc    2040
attcgattcc tgtttgtaat tgtccttta acagcgatcg cgtatttcgt ctcgctcagg    2100
cgcaatcacg aatgaataac ggtttggttg atgcgagtga ttttgatgac gagcgtaatg    2160
gctggcctgt tgaacaagtc tggaaagaaa tgcataagct tttgccattc tcaccggatt    2220
cagtcgtcac tcatggtgat ttctcacttg ataaccttat ttttgacgag gggaaattaa    2280
taggttgtat tgatgttgga cgagtcggaa tcgcagaccg ataccaggat cttgccatcc    2340
tatggaactg cctcggtgag ttttctcctt cattacagaa acggcttttt caaaaatatg    2400
gtattgataa tcctgatatg aataaattgc agtttcattt gatgctcgat gagttttct     2460
aaccctgatc actgtggaat gtgtgtcagt tagggtgtgg aaagtcccca ggctccccag    2520
caggcagaag tatgcaaagc atgcatctca attagtcagc aaccaggtgt ggaaagtccc    2580
caggctcccc agcaggcaga gtatgcaaa gcatgcatct caattagtca gcaaccatag    2640
tcccgcccct aactccgccc atcccgcccc taactccgcc cagttacggg gtcattagtt    2700
catagcccat atatggagtt ccgcgttaca taacttacgg taaatggccc gcctggctga    2760
ccgcccaacg acccccgccc attgacgtca ataatgacgt atgttcccat agtaacgcca    2820
atagggactt tccattgacg tcaatgggtg gagtatttac ggtaaactgc ccacttggca    2880
gtacatcaag tgtatcatat gccaagtacg cccctattg acgtcaatga cggtaaatgg    2940
cccgcctggc attatgccca gtacatgacc ttatgggact ttcctacttg gcagtacatc    3000
tacgtattag tcatcgctat taccatggtg atgcggtttt ggcagtacat caatgggcgt    3060
ggatagcggt ttgactcacg ggatttcca agtctccacc ccattgacgt caatgggagt    3120
ttgttttggc accaaaatca acgggacttt ccaaaatgtc gtaacaactc cgccccattg    3180
acgcaaatgg gcggtaggcg tgtacggtgg gaggtctata taagcagagc tcgtttagtg    3240
aaccgtcaga tcgcctggag acgccatcca cgctgttttg acctccatag aagacaccgg    3300
gaccgatcca gcctccgcgg ctcgcatctc tccttcacgc gcccgccgcc ctacctgagg    3360
ccgccatcca cgccggttga gtcgcgttct gccgcctccc gcctgtggtg cctcctgaac    3420
```

| | |
|---|---|
| tgcgtccgcc gtctaggtaa gtttaaagct caggtcgaga ccgggccttt gtccggcgct | 3480 |
| cccttggagc ctaccctagac tcagccggct ctccacgctt tgcctgaccc tgcttgctca | 3540 |
| actctagttc tctcgttaac ttaatgagac agatagaaac tggtcttgta gaaacagagt | 3600 |
| agtcgcctgc ttttctgcca ggtgctgact tctctcccct gggcttttt cttttctca | 3660 |
| ggttgaaaag aagaagacga agaagacgaa gaagacaaag ccgccaccat ggatgcaatg | 3720 |
| aagagagggc tctgctgtgt gctgctgctg tgtggagcag tcttcgtttc gcccagcggt | 3780 |
| accggatccg tcgacggggg gagatctttt tccctctgcc aaaaattatg gggacatcat | 3840 |
| gaagcccctt gagcatctga cttctggcta ataaaggaaa tttattttca ttgcaatagt | 3900 |
| gtgttggaat ttttgtgtc tctcactcgg aaggacataa gggcggccgc tagc | 3954 |

<210> SEQ ID NO 13
<211> LENGTH: 3876
<212> TYPE: DNA
<213> ORGANISM: Artificial Sequence
<220> FEATURE:
<223> OTHER INFORMATION: Description of Artificial Sequence: NTC7482

<400> SEQUENCE: 13

| | |
|---|---|
| ccgcctaatg agcgggcttt ttttctctag gctgcctcgc gcgtttcggt gatgacggtg | 60 |
| aaaacctctg acacatgcag ctcccggaga cggtcacagc ttgtctgtaa gcggatgccg | 120 |
| ggagcagaca agcccgtcag ggcgcgtcag cgggtgttgg cgggtgtcgg ggcgcagcca | 180 |
| tgacccagtc acgtagcgat agcggagtgt atactggctt aactatgcgg catcagagca | 240 |
| gattgtactg agagtgcacc atatgcggtg tgaaataccg cacagatgcg taaggagaaa | 300 |
| ataccgcatc aggcgctctt ccgcttcctc gctcactgac tcgctgcgct cggtcgttcg | 360 |
| gctgcggcga gcggtatcag ctcactcaaa ggcggtaata cggttatcca gaatcagg | 420 |
| ggataacgca ggaaagaaca tgtgagcaaa aggccagcaa aaggccagga accgtaaaaa | 480 |
| ggccgcgttg ctggcgtttt tccataggct ccgcccccct gacgagcatc acaaaaatcg | 540 |
| acgctcaagt cagaggtggc gaaacccgac aggactataa agataccagg cgtttccccc | 600 |
| tggaagctcc ctcgtgcgct ctcctgttcc gaccctgccg cttaccggat acctgtccgc | 660 |
| cttctccct tcgggaagcg tggcgctttc tcatagctca cgctgtaggt atctcagttc | 720 |
| ggtgtaggtc gttcgctcca agctgggctg tgtgcacgaa ccccccgttc agcccgaccg | 780 |
| ctgcgcctta tccggtaact atcgtcttga gtccaacccg gtaagacacg acttatcgcc | 840 |
| actggcagca gccactggta acaggattag cagagcgagg tatgtaggcg gtgctacaga | 900 |
| gttcttgaag tggtggccta actacggcta cactagaaga acagtatttg gtatctgcgc | 960 |
| tctgctgaag ccagttacct tcggaaaaag agttggtagc tcttgatccg gcaaacaaac | 1020 |
| caccgctggt agcggtggtt tttttgtttg caagcagcag attacgcgca gaaaaaaagg | 1080 |
| atctcaagaa gatcctttga tcttttctac ggggtctgac gctcagtgga acgaaaactc | 1140 |
| acgttaaggg attttggtca tgagattatc aaaaaggatc ttcacctaga tccttttaaa | 1200 |
| ttaaaaatga agttttaaat caatctaaag tatatatgag taaacttggt ctgacagtta | 1260 |
| ccaatgctta atcagtgagg cacctatctc agcgatctgt ctatttcgtt catccatagt | 1320 |
| tgcctgactc ctgcaaacca cgttgtgtct caaaatctct gatgttacat tgcacaagat | 1380 |
| aaaaatatat catcatgaac aataaaactg tctgcttaca taacagtaa tacaaggggt | 1440 |
| gttatgagcc atattcaacg ggaaacgtct tgctcgaggc cgcgattaaa ttccaacatg | 1500 |
| gatgctgatt tatatgggta taaatgggct cgcgataatg tcgggcaatc aggtgcgaca | 1560 |

```
atctatcgat tgtatgggaa gcccgatgcg ccagagttgt ttctgaaaca tggcaaaggt    1620
agcgttgcca atgatgttac agatgagatg gtcagactaa actggctgac ggaatttatg    1680
cctcttccga ccatcaagca ttttatccgt actcctgatg atgcatggtt actcaccact    1740
gcgatcccg ggaaaacagc attccaggta ttagaagaat atcctgattc aggtgaaaat     1800
attgttgatg cgctggcagt gttcctgcgc cggttgcatt cgattcctgt ttgtaattgt    1860
ccttttaaca gcgatcgcgt atttcgtctc gctcaggcgc aatcacgaat gaataacggt    1920
ttggttgatg cgagtgattt tgatgacgag cgtaatggct ggcctgttga acaagtctgg    1980
aaagaaatgc ataagctttt gccattctca ccggattcag tcgtcactca tggtgatttc    2040
tcacttgata accttatttt tgacgagggg aaattaatag gttgtattga tgttggacga    2100
gtcggaatcg cagaccgata ccaggatctt gccatcctat ggaactgcct cggtgagttt    2160
tctccttcat tacagaaacg gcttttcaa aaatatggta ttgataatcc tgatatgaat     2220
aaattgcagt ttcatttgat gctcgatgag ttttctaac cctgatcact gtggaatgtg     2280
tgtcagttag ggtgtggaaa gtccccaggc tccccagcag gcagaagtat gcaaagcatg    2340
catctcaatt agtcagcaac caggtgtgga aagtccccag gctccccagc aggcagaagt    2400
atgcaaagca tgcatctcaa ttagtcagca accatagtcc cgcccctaac tccgcccatc    2460
ccgcccctaa ctccgcccag gatccgctct agatggccat tgcatacgtt gtatccatat    2520
cataatatgt acatttatat tggctcatgt ccaacattac cgccatgttg acattgatta    2580
ttgactagtt attaatagta atcaattacg gggtcattag ttcatagccc atatatggag    2640
ttccgcgtta cataacttac ggtaaatggc ccgcctggct gaccgcccaa cgaccccgc     2700
ccattgacgt caataatgac gtatgttccc atagtaacgc caatagggac tttccattga    2760
cgtcaatggg tggagtattt acggtaaact gcccacttgg cagtacatca agtgtatcat    2820
atgccaagta cgccccctat tgacgtcaat gacggtaaat ggcccgcctg gcattatgcc    2880
cagtacatga ccttatggga ctttcctact tggcagtaca tctacgtatt agtcatcgct    2940
attaccatgg tgatgcggtt ttggcagtac atcaatgggc gtggatagcg gtttgactca    3000
cggggatttc caagtctcca ccccattgac gtcaatggga gtttgttttg gcaccaaaat    3060
caacgggact ttccaaaatg tcgtaacaac tccgccccat tgacgcaaat gggcggtagg    3120
cgtgtacggt gggaggtcta tataagcaga gctcgtttag tgaaccgtca gatcgcctgg    3180
agacgccatc cacgctgttt tgacctccat agaagacacc gggaccgatc cagcctccgc    3240
ggctcgcatc tctccttcac gcgcccgccg ccctacctga gccgccatc acgccggtt     3300
gagtcgcgtt ctgccgcctc ccgcctgtgg tgcctcctga actgcgtccg ccgtctaggt    3360
aagtttaaag ctcaggtcga gaccgggcct ttgtccggcg ctcccttgga gcctacctag    3420
actcagccgg ctctccacgc tttgcctgac cctgcttgct caactctagt tctctcgtta    3480
acttaatgag acagatagaa actggtcttg tagaaacaga gtagtcgcct gcttttctgc    3540
caggtgctga cttctctccc ctgggctttt ttcttttct caggttgaaa agaagaagac     3600
gaagaagacg aagaagacaa agccgccacc atggatgcaa tgaagagagg gctctgctgt    3660
gtgctgctgc tgtgtggagc agtcttcgtt tcgcccagcg gtaccggatc cgtcgacggg    3720
gggagatctt tttccctctg ccaaaaatta tggggacatc atgaagcccc ttgagcatct    3780
gacttctggc taataaagga aatttatttt cattgcaata gtgtgttgga atttttgtg     3840
tctctcactc ggaaggacat aagggcggcc gctagc                              3876
```

```
<210> SEQ ID NO 14
<211> LENGTH: 87
<212> TYPE: DNA
<213> ORGANISM: Artificial Sequence
<220> FEATURE:
<223> OTHER INFORMATION: Description of Artificial Sequence: NTC8482,
      NTC8682, NTC7482, NTC7682 optimized TPA-SalI secretion signal

<400> SEQUENCE: 14
atggatgcaa tgaagagagg gctctgctgt gtgctgctgc tgtgtggagc agtcttcgtt    60
tcgcccagcg gtaccggatc cgtcgac                                        87
```

DNA PLASMIDS WITH IMPROVED COPY NUMBER

CROSS REFERENCE TO RELATED APPLICATIONS

This application claims priority to U.S. Provisional Patent Application Ser. No. 61/205,561, entitled "DNA Plasmids With Improved Copy Number" which was filed Jan. 21, 2009, the entire contents of which are incorporated herein by reference.

STATEMENT REGARDING FEDERALLY SPONSORED RESEARCH OR DEVELOPMENT

This invention was supported in part with government support under Grant No. 2 R44 GM072141-02, awarded by the National Institutes of Health. The government has certain rights in this invention.

FIELD OF THE INVENTION

The present invention relates to the production of covalently closed circular (ccc) recombinant DNA molecules such as plasmids, cosmids, bacterial artificial chromosomes (BACs), bacteriophages, viral vectors and hybrids thereof, and more particularly to vector modifications that improve production yield of said DNA molecules in fermentation culture. Such recombinant DNA molecules are useful in biotechnology, transgenic organisms, gene therapy, therapeutic vaccination, agriculture and DNA vaccines.

BACKGROUND OF THE INVENTION

*E. coli* plasmids have long been an important source of recombinant DNA molecules used by researchers and by industry. Today, plasmid DNA is becoming increasingly important as the next generation of biotechnology products (e.g., gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines. Plasmids are also utilized in gene therapy or gene replacement applications, wherein the desired gene product is expressed from the plasmid after administration to the patient.

Therapeutic plasmids often contain a pMB1, ColE1 or pBR322 derived replication origin. Common high copy number derivatives have mutations affecting copy number regulation, such as rop (Repressor of primer gene) deletion, with a second site mutation that increases copy number (e.g. pMB1 pUC G to A point mutation, or ColE1 pMM1). Higher temperature (42° C.) can be employed to induce selective plasmid amplification with pUC and pMM1 replication origins.

Published Application WO2006023546 (Carnes, A E and Williams, J A) disclose methods for fed-batch fermentation, in which plasmid-containing *E. coli* cells were grown at a reduced temperature during part of the fed-batch phase, during which growth rate was restricted, followed by a temperature up-shift and continued growth at elevated temperature in order to accumulate plasmid; the temperature shift at restricted growth rate improved yield and purity of plasmid. Other fermentation processes for plasmid production are described in Carnes A. E. *BioProcess Intl* 2005; 3:36-44, which is incorporated herein by reference in its entirety.

There is a significant need for methods that increase production yield of plasmid DNA. High specific yields are very desirable since increased plasmid yield per gram of bacteria, or increased plasmid relative to genomic DNA, lead directly to higher final product purities. Further improvements in yield or increases in the percentage plasmid per total DNA would further decrease production cost, improve purity and simplify removal of genomic DNA (gDNA).

SUMMARY OF THE INVENTION

The present invention relates generally to methods of increasing production yield of covalently closed super-coiled plasmid DNA.

One object of the invention is to provide improved copy number plasmid vectors. Yet another object of the invention is to provide methods for improving plasmid copy number.

According to one object of the invention, a method of increasing production yield of covalently closed super-coiled plasmid DNA comprises modifying the plasmid DNA to add one or more components selected from the group consisting of an SV40 enhancer, PAS-BH region, and PAS; transforming the modified plasmid DNA into a bacterial cell line rendered competent for transformation; and isolating the resultant transformed bacterial cells.

According to another object of the invention, said methods of plasmid modification improve plasmid yield in subsequent shake flask and or fermentation culture.

According to yet another object of the invention, a method of increasing production yield of covalently closed super-coiled plasmid DNA comprises modifying the plasmid DNA to remove one or more transcriptional terminators; transforming the modified plasmid DNA into a bacterial cell line rendered competent for transformation; and isolating the resultant transformed bacterial cells.

It is another object of the present invention to provide compositions of matter for construction of a vector.

According to one object of the invention, a composition for construction of a vector comprises an SV40 enhancer with at least 90% sequence identity to the sequence set forth as SEQ ID NO: 2, and a plasmid DNA replicon, wherein said SV40 enhancer is operably linked to said plasmid DNA replicon. According to another object of the invention, said SV40 enhancer improves plasmid yield in subsequent shake flask and or fermentation culture. According to still another object of the invention, said vector has at least 95% sequence identity to a sequence selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

Yet another object of the invention provides a composition for construction of a vector, comprising a PAS-BH site with at least 90% sequence identity to the sequence set forth as SEQ ID NO: 3, and a plasmid DNA replicon, wherein said PAS-BH site is operably linked to said plasmid DNA replicon. According to another object of the invention, said PAS-BH site improves plasmid yield in subsequent shake flask and or fermentation culture. Furthermore, another object of the invention provides that said vector has at least 95% sequence identity to a sequence selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

Still another object of the invention provides a composition for construction of a vector, comprising a PAS-BH region with at least 90% sequence identity to the sequence set forth as SEQ ID NO: 4, and a plasmid DNA replicon, wherein said PAS-BH region is operably linked to said plasmid DNA replicon. According to another object of the invention, said PAS-BH region improves plasmid yield in subsequent shake flask and or fermentation culture. Furthermore, another object of the invention provides that said vector has at least 95% sequence identity to a sequence selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

Further objects and advantages of the invention will become apparent from a consideration of the drawings and ensuing description.

DETAILED DESCRIPTION OF THE PREFERRED EMBODIMENTS

Figure 1:
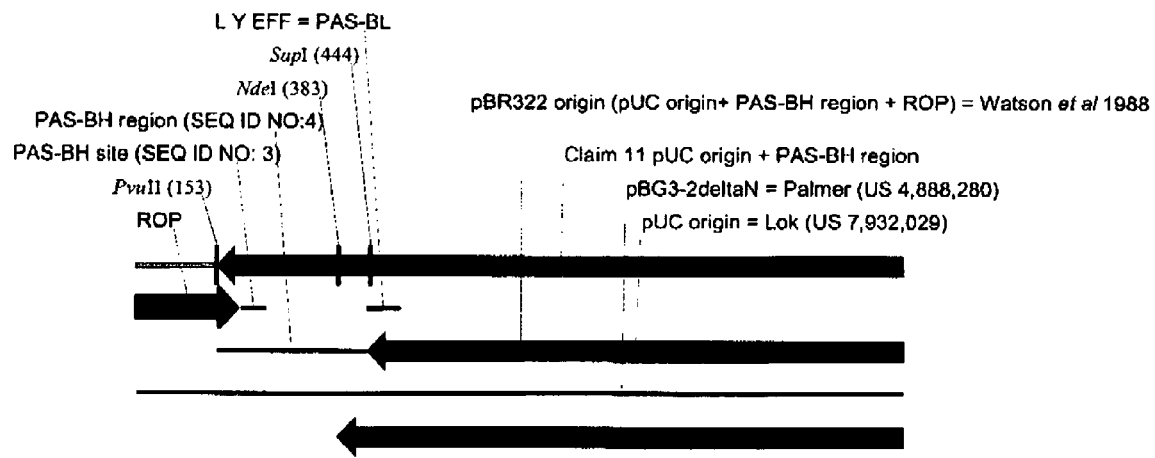
FIG. 1 depicts pNTCUltra1 PAS-BH.

The invention relates generally to plasmid DNA compositions and methods to improve plasmid copy number. The invention can be practiced to improve the copy number of vectors such as eukaryotic expression plasmids useful for gene therapy, genetic immunization and or interferon therapy. It is to be understood that all references cited herein are incorporated by reference in their entirety.

According to one preferred embodiment, the present invention provides for method of increasing production yield of covalently closed super-coiled plasmid DNA, which comprises modifying the plasmid DNA to add one or more components selected from the group consisting of an SV40 enhancer, PAS-BH region, and PAS; transforming the modified plasmid DNA into a bacterial cell line rendered competent for transformation; and isolating the resultant transformed bacterial cells.

According to another preferred embodiment, a method of increasing production yield of covalently closed super-coiled plasmid DNA comprises modifying the plasmid DNA to remove one or more transcriptional terminators; transforming the modified plasmid DNA into a bacterial cell line rendered competent for transformation; and isolating the resultant transformed bacterial cells.

In one preferred embodiment, a SV40 enhancer is incorporated into a plasmid DNA backbone to improve plasmid copy number. In another preferred embodiment, a fragment of the pBR322 origin containing a primosomal assembly site is incorporated into a plasmid DNA backbone to improve plasmid copy number. In yet another preferred embodiment, a SV40 enhancer and a fragment of the pBR322 origin containing a primosomal assembly site are both incorporated into a plasmid DNA backbone to improve plasmid copy number.

The methods of plasmid modification of the present invention have been surprisingly found to improve plasmid yield in subsequent shake flask and or fermentation culture.

Plasmid copy number is preferably increased by employing specific constructs or compositions incorporated in a vector. According to one preferred embodiment, the present invention provides a composition for construction of a vector, comprising an SV40 enhancer with at least 90% sequence identity to the sequence set forth as SEQ ID NO: 2, and a plasmid DNA replicon, wherein the SV40 enhancer is operably linked to the plasmid DNA replicon. It has been surprisingly found that this SV40 enhancer improves plasmid yield in subsequent shake flask and or fermentation culture. According to another preferred embodiment, the vector has at least 95% sequence identity to a sequence selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

As used herein, the term "sequence identity" refers to the degree of identity between any given query sequence, e.g., SEQ ID NO: 2, and a subject sequence. A subject sequence may, for example, have at least 90 percent, at least 95 percent, or at least 99 percent sequence identity to a given query sequence. To determine percent sequence identity, a query sequence (e.g., a nucleic acid sequence) is aligned to one or more subject sequences using any suitable sequence alignment program that is well known in the art, for instance, the computer program ClustalW (version 1.83, default parameters), which allows alignments of nucleic acid sequences to be carried out across their entire length (global alignment). Chema et al., *Nucleic Acids Res.*, 31(13):3497-500 (2003). In a preferred method, the sequence alignment program (e.g., ClustalW) calculates the best match between a query and one or more subject sequences, and aligns them so that identities, similarities, and differences can be determined. Gaps of one or more nucleotides can be inserted into a query sequence, a subject sequence, or both, to maximize sequence alignments. For fast pair-wise alignments of nucleic acid sequences, suitable default parameters can be selected that are appropriate for the particular alignment program. The output is a sequence alignment that reflects the relationship between sequences. To further determine percent identity of a subject nucleic acid sequence to a query sequence, the sequences are aligned using the alignment program, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

According to another preferred embodiment, the present invention provides a composition for construction of a vector, comprising a PAS-BH site with at least 90% sequence identity to the sequence set forth as SEQ ID NO: 3, and a plasmid DNA replicon, wherein the PAS-BH site is operably linked to the plasmid DNA replicon. It has been surprisingly found that this PAS-BH site improves plasmid yield in subsequent shake flask and or fermentation culture. According to another preferred embodiment, the vector has at least 95% sequence identity to a sequence selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

According to another preferred embodiment, the present invention provides a composition for construction of a vector, comprising a PAS-BH region with at least 90% sequence identity to the sequence set forth as SEQ ID NO: 4, and a plasmid DNA replicon, wherein said PAS-BH region is operably linked to said plasmid DNA replicon. It has been surprisingly found that this PAS-BH region improves plasmid yield in subsequent shake flask and or fermentation culture. According to another preferred embodiment, the vector preferably has at least 95% sequence identity to a sequence selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

Turning now to the drawings, FIG. 1. shows an annotated map of the pNTCUltra1 PAS-BH vector with the locations of the PAS-BH primosomal assembly site, SV40 enhancer and other key elements indicated.

Figure 2:
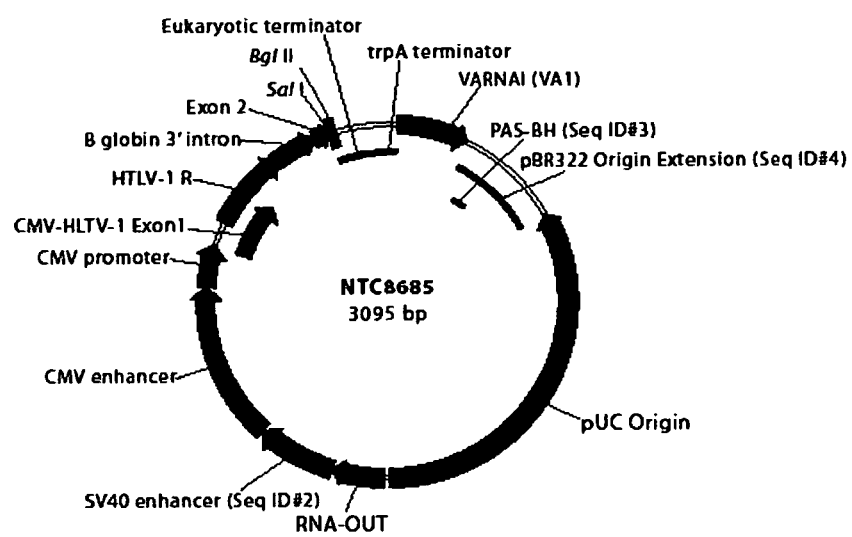
FIG. 2 depicts NTC8685.

FIG. 2 shows an annotated map of the antibiotic-free NTC8685-EGFP vector with the locations of the PAS-BH primosomal assembly site, SV40 enhancer and other key elements indicated.

Figure 3:
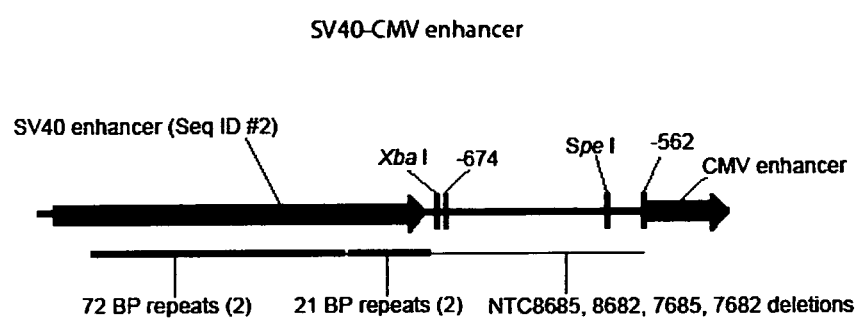
FIG. 3 depicts SV40-CMV enhancer.
Table 1: SV40 enhancer and PAS-BH improve plasmid yields
Table 2: Antibiotic-free vector expression and manufacture
Table 3: NTC8682, NTC8482, NTC7682, NTC7482, NTC8685, NTC8485, NTC7685, and NTC7485 vectors.
SEQ ID NO:1: pNTCUltra1 PAS-BH
SEQ ID NO:2: SV40 enhancer
SEQ ID NO:3: PAS-BH
SEQ ID NO:4: pBR322 origin region between ROP and PAS-BL (pBR322 2067-2351)
SEQ ID NO:5: Apal-Kpnl dual terminator
SEQ ID NO:6: NTC8685
SEQ ID NO:7: NTC8485
SEQ ID NO:8: NTC8682
SEQ ID NO:9: NTC8482
SEQ ID NO:10: NTC7685
SEQ ID NO:11: NTC7485
SEQ ID NO:12: NTC7682
SEQ ID NO:13: NTC7482
SEQ ID NO:14: NTC8482, NTC8682, NTC7482, NTC7682 optimized TPA-SalI secretion signal
Definition of Terms
AF: Antibiotic-free
bp: basepairs
ccc: Covalently Closed Circular
DNA replicon: A genetic element that can replicate under its own control; examples include plasmids, cosmids, bacterial artificial chromosomes (BACs), bacteriophages, viral vectors and hybrids thereof.
E. coli: Escherichia coli, a gram negative bacteria
g: Gram, kg for kilogram
kan: Kanamycin
kanR: Kanamycin Resistance gene
kozak sequence: Optimized sequence of consensus DNA sequence gccRccATG (R=G or A) immediately upstream of an ATG start codon that ensures efficient tranlation initiation. A SalI site (GTCGAC) immediately upstream of the ATG start codon (GTCGACATG) is an effective Kozak sequence
$OD_{600}$: optical density at 600 nm
PAS: Primosomal assembly site
PAS-BH: Primosomal assembly site on the heavy (leading) strand (SEQ ID NO:3)
PAS-BH region: pBR322 origin region between ROP and PAS-BL (approximately pBR322 2067-2351; SEQ ID NO:4)
PAS-BH: Primosomal assembly site on the light (lagging) strand
PCR: Polymerase Chain Reaction
Plasmid: An extra chromosomal DNA molecule separate from the chromosomal DNA which is capable of replicating independently from the chromosomal DNA.
Primosomal assembly site: DNA sequence that binds priA, which, in turn, recruits the remaining proteins to form the preprimosome [priB, dnaT, recruits dnaB (delivered by dnaC)], which then also recruits primase (dnaG), which then, finally, makes a short RNA substrate for DNA polymerase I
pUC origin: pBR322-derived origin, with G to A transition that increases copy number at elevated temperature
pUC plasmid: Plasmid containing the pUC origin
SV40 enhancer: Region containing the 72 by and optionally the 21 by repeats (SEQ ID NO:2; see FIG. 3)
Transcription terminator: A DNA sequence that marks the end of a gene or operon for transcription. This may be an intrinsic transcription terminator or a Rho-dependent transcriptional terminator. For an intrinsic terminator, such as the trpA terminator, a hairpin structure forms within the transcript that disrupts the mRNA-DNA-RNA polymerase ternary complex. The dual terminator in pNTCUltra1-term+ contains two intrinsic terminators, the fd gene VIII terminator and the tonB bidirectional terminator. Alternatively, Rho-dependent transcriptional terminators require Rho factor, an RNA helicase protein complex, to disrupt the nascent mRNA-DNA-RNA polymerase ternary complex.
vector: A gene delivery vehicle, including viral (e.g. alphavirus, poxvirus, lentivirus, retrovirus, adenovirus, adenovirus related virus, etc.) and nonviral (e.g. plasmid, midge, transcriptionally active PCR fragment, minicircles, bacteriophage, etc.) vectors. These are well known in the art and are included herein by reference.

FIG. 3 shows an annotated map of the SV40-CMV enhancer region in the pNTCUltra1 PAS-BH and NTC8682, NTC8482, NTC7682, NTC7482, NTC8685, NTC8485, NTC7685, and NTC7485 vector backbones with locations of the SV40 enhancer 72 by and 21 by repeats (SEQ ID NO:2), the start of the CMV enhancer and the CMV upstream region deletion in the NTC8685, NTC8682, NTC7685, NTC7682 vectors shown. Coordinates −674 and −562 in the CMV upstream region are relative to the CMV transcription start site.

The invention also relates to compositions and methods for producing high copy plasmids using the gram negative bacterium *E. coli* as a production host. The present invention provides sequences that, when introduced into a vector backbone, increase plasmid copy number.

We disclose herein the surprising observation that a SV40 enhancer can be utilized as a plasmid copy number enhancer. We further disclose the surprising observation that plasmid copy number is improved by addition of a previously considered nonfunctional region of the pBR322 origin. This region is not present in pUC plasmids.

As described herein, plasmid copy number is increased by addition of an SV40 enhancer to the plasmid backbone. In yet another preferred embodiment, the SV40 enhancer is inserted upstream of the eukaryotic promoter. In yet another preferred embodiment, the SV40 enhancer is included as a chimeric SV40-CMV promoter. In yet another preferred embodiment, the SV40 enhancer comprises one or more copies of the 72 by enhancer.

In yet another preferred embodiment, plasmid copy number is increased by addition of part or all of the pBR322 origin from between the ROP and PAS-BL site to the plasmid backbone. In yet another preferred embodiment, the pBR322 origin region is inserted upstream of the eukaryotic promoter. In yet another preferred embodiment, the origin region is included as an extended pUC origin. In yet another preferred embodiment, the pBR322 origin region contains the PAS-BH site. In yet another preferred embodiment, the additional origin region is from pBR322 coordinates 2067-2351 (GenBank Accession #: J01749).

In another preferred embodiment, plasmid copy number is increased by removal of transcriptional terminator sequences from the plasmid backbone.

EXAMPLES

The methods of the invention are further illustrated by the following examples. These are provided by way of illustration and are not intended in any way to limit the scope of the invention.

Example 1

Development of kanR Plasmid Vectors with Improved Copy Number

NTCUltra1=6544 by NTC7164-hmPA-EGFP (SV40-CMV promoter, ubiquitin targeting vector, anthrax protective antigen). The SV40-CMV promoter and ubiquitin targeting vectors are disclosed in Williams, J A 2006 World Patent Application WO2006078979 and included herein by reference in their entirety.

The pNTCUltra1-term+ plasmid contains a 100 by ApaI-KpnI dual terminator containing the fd gene VIII terminator-tonB bidirectional terminator of the following sequence:

SEQ ID NO:5: 100 by ApaI-KpnI dual terminator

GGGCCCACCGATACAATTAAAGGCTCCTTTTGGAGCCTTTTTTTTGGAC

TGCAAACAAATAGTCAAAAGCCTCCGGTCGGAGGCTTTTGACTTTGGTAC

C.

ApaI (GGGCCC) and KpnI (GGTACC) DNA sequence is shown. The underlined dual terminator sequence is not present in pNTCUltra1.

pNTCUltra1-PAS-BH=6826 by NTCUltra1 derivative contains the pUC19 replication origin with an additional 285 by of pBR322 origin (starting at the Pvull site immediately downstream of the ROP gene; pBR322 coordinates 2067-2351; SEQ ID NO:4) that includes the 48 by PAS-BH site (SEQ ID NO:3).

pNTCUltra1 (-SV40) has the SV40 enhancer deleted (by removal of the 324 by ApaI-XbaI term-SV40 enhancer region from pNTCUltra1-term+; this region contains two copies of the SV40 72 by repeat).

pNTCUltra4-PAS-BH=5895 by vector substitutes the PAS-BH containing region of the pBR322 origin for the SV40 enhancer upstream of CMV promoter.

pNTCUltra4=the PAS-BH containing region of the pBR322 origin is deleted from pNTCUltra4-PAS-BH

Example 2

Plasmid Fermentation and Analytical Evaluation

Fermentation: Fermentations were performed using proprietary fed-batch media (NTC3019) in New Brunswick Bio-Flo 110 bioreactors as described (Carnes and Williams, Supra, 2006). The seed cultures were started from glycerol stocks or colonies and streaked onto LB medium agar plates containing 50 µg/mL kanamycin. The plates were grown at 30° C.; cells were resuspended in media, and used to provide approximately 0.1% inoculums for the fermentations.

Fermentations were performed with E. coli strain DH5α [F-φ80dlacZΔM15 Δ(lacZYA-argF) U169 recA1 endA1 hsdR17(rk−, mk+) phoA supE44 λthi-1 gyrA96 relA1]. Antibiotic-free RNA-OUT plasmid fermentations were performed in DH5α strains containing chromosomally integrated pCAH63-CAT RNA-IN-SacB (P5/6 6/6) as disclosed in Williams, J A 2008 World Patent Application WO2008153733. SacB (Bacillus subtilis levansucrase) is a counterselectable marker which is lethal to E. coli cells in the presence of sucrose. Translation of SacB from the RNA-IN-SacB transcript is inhibited by plasmid encoded RNA-OUT. This facilitates plasmid selection in the presence of sucrose, by inhibition of SacB mediated lethality.

Analytical Methods: Culture samples were taken at key points and at regular intervals during all fermentations. Samples were analyzed immediately for biomass ($OD_{600}$) and for plasmid yield. Plasmid yield was determined by quantification of plasmid obtained from Qiagen Spin Miniprep Kit preparations as described (Carnes and Williams, Supra, 2006). Briefly, cells were alkaline lysed, clarified, plasmid was column purified, and eluted prior to quantification. Agarose gel electrophoresis analysis (AGE) was performed on 0.8-1% Tris/acetate/EDTA (TAE) gels as described in Carnes and Williams, supra, 2006.

Example 3

Plasmid Vectors Containing PAS-BH and/or the SV40 Enhancer have Improved Copy Number In the process of developing high yielding vector backbones, sequences that dramatically and surprisingly affect yield were observed, and are described below.

Positioning of Prokaryotic Terminator Sequences

A pNTCUltra1 plasmid, with a dual terminator sequence inserted upstream of the SV40 enhancer (pNTCUltra1-term+), was inexplicably a poor producer. The slow growth, poor induction and low overall yield of 119 mg/L at harvest (2.5 mg plasmid/L/$OD_{600}$) was in contrast to the control pNTCUltra1 plasmid without the terminator region (Table 1: RF157, 1930 mg/L, 17.3 mg plasmid/L/$OD_{600}$). Improving plasmid copy number by removing transcription terminators was surprising and unexpected.

TABLE 1

SV40 enhancer and PAS-BH improve plasmid yields

| Fermentation† | Vector | Modification | Fermentation yield (mg/L) | Fermentation specific yield (mg/L/$OD_{600}$) |
|---|---|---|---|---|
| RF157 | pNTCUltra1 | SV40-CMV | 1930 | 17.3 |
| RF158 | pNTCUltra1 (−SV40) | CMV | 1050 | 9.9 |
| RF160 | pNTCUltra1-PAS-BH | SV40-CMV | 2210 | 22.9 |
| RF167++ | | +PAS-BH origin | 2220++ | 25.3++ |
| RF154 | pNTCUltra4-PAS-BH | PAS-BH-CMV | 1230 | 12.3 |
| RF161 | pNTCUltra4 | CMV | 800 | 10.2 |
| RF164 | gWIZ-D | PAS-BH-CMV | 1210 | 14.4 |

†All fermentations induced at 50 $OD_{600}$ for 10.5 h at 42° C., 1 h 25° C. hold
++12 h induction, final yield was 51 mg plasmid/g DCW SV40 Enhancer (SEQ ID NO:2)

Surprisingly, the pNTCUltra1 vector yielded approximately twice the production yield of gWiz-derived (gWIZ-D) plasmids (Genlantis, San Diego Calif.) (Table 1, RF157 versus RF164). The pNTCUltra improvement compared to gWiz was not insert-specific, and yields in these ranges were obtained with a variety of insert sequences within these vector backbones. These vectors are both eukaryotic expression vectors containing the same elements in different orientations; pUC origin, a kanR selectable marker, and a eukaryotic expression cassette comprising the CMV promoter-gene of interest-eukaryotic terminator. Deletion analysis surprisingly demonstrated that the SV40 enhancer in pNTCUltra1 (SEQ ID NO:2) was critical for improved productivity (Table 1; RF157 versus RF158). The use of the SV40 enhancer to improve plasmid copy number was surprising and unexpected.

pBR322 Origin Region 2067-2351 (SEQ ID NO:4)

Therapeutic plasmids such as VR1012 (Vical) and derivative gWIZ (Gene Therapy Systems), pPJV7563 (PowderMed/Pfizer), V1JNS (Merck), pVAX1 (Invitrogen), pLL14 (Merial), and pNTCUltra1 (Nature Technology Corporation) were all constructed using origin regions derived from high copy pUC plasmids. To increase copy number, these vectors all deleted the Repressor of primer (ROP) gene. The ROP deletion also includes a leading strand primosomal assembly site (PAS-BH) present in pBR322 (Marians K J, Soeller W, Zipursky S L. 1982. *J. Biol. Chem.* 257: 5656-5662). This site is presumed nonfunctional, since 1) the ROP deletion including PAS-BH dramatically increases copy number and 2) Deletion of PAS-BH does not dramatically affect plasmid replication in vivo (Masai H, Arai K I. 1989. *J. Bacteriol.* 171: 2975-2980). A more precise deletion of the ROP gene (ROP only deletion, includes pBR322 region 2067-2351 compared to the pUC origin ROP +PAS-BH deletion) was constructed (pNTCUltra1 PAS-BH; FIG. 1; SEQ ID NO:1) and evaluated for plasmid copy number. Surprisingly, extension of the pUC promoter to include the deleted 285 bp region of pBR322 (SEQ ID NO:4) including PAS-BH (SEQ ID NO:3) further improved productivity (Table 1; RF160 versus RF157) up to 2220 mg/L and 25.3 mg/L/$OD_{600}$(51 mg/gDCW) with a 12 hr induction (Table 1; RF167). While not limiting the application of the invention, improved yields may be due to PAS-BH mediated enhanced primosomal assembly on the leading strand when it is within the DNA polymerase I replication region. Alternatively, another functional region unrelated to PAS-BH or primosomal assembly may be present in this region. Interestingly, yield improvement was also observed in plasmids containing the PAS-BH site 3 kb downstream of the origin (Table 1 RF154, pNTCUltra4 PAS-BH-CMV versus RF161, CMV).

pNTCUltra1-PAS-BH and 1VTC7482-41H-HA

In summary, a vector backbone, pNTCUltra1, was identified that is twice the productivity of previously characterized high-yielding vectors such as pVAX1 and gWiz. Productivity enhancement was surprisingly determined to be due to a SV40 enhancer present in the pNTCUltra1 vector. Productivity was further improved by inclusion of a leading-strand primosomal assembly site in the vector, downstream of the replication origin (pNTCUltra1-PAS-BH; FIG. 1). This enhancement is also observed with NTC7482-41H-HA compared to gWIZ (Table 2). NTC7482-41H-HA has the same vector backbone as pNTCUltra1, but different transgene sequences. This demonstrates that the enhancement is not affected by alterations to the eukaryotic portion of the vector.

Example 4

Antibiotic-free Plasmid Vectors Containing PAS-BH and/or the SV40 Enhancer have Improved Copy Number The NTC8385, NTC8485 and NTC8685 plasmids are antibiotic-free vectors that contain a short regulatory RNA (RNA-OUT) in place of the antibiotic resistance marker (kanR). The creation and application of RNA-OUT based antibiotic-free vectors is disclosed in Williams, Supra, 2008 and are included herein by reference.

NTC8485 (SEQ ID NO:7) has the equivalent SV40 and PAS-BH backbone as pNTCUltra1-PAS-BH and NTC7482-41H-HA. NTC8685 (FIG. 2; SEQ ID NO:6) has the equivalent SV40 and PAS-BH backbone as pNTCUltra1-PAS-BH and NTC7482-41H-HA and additionally incorporates a deletion of sequences between the SV40 enhancer and the CMV promoter (FIG. 3). This deletion is the only difference between NTC8485 and NTC8685. NTC8385 (Williams, Supra, 2008) is an equivalent antibiotic-free vector without the SV40 and PAS-BH regions. The fermentation yield of NTC8485 (RF248) and NTC8685 (RF252) was significantly improved relative to NTC8385 (RF247; Table 2). This was observed as both an increase in specific yield (a measure of plasmid amount per cell) and specific yield/size (a measure of plasmid copy number per cell) (Table 2). The improved yield was not at the expense of eukaryotic cell expression which is highest with the NTC8685 backbone (Table 2). This also demonstrates that improved copy number is not dependent on the kanR gene since it was observed with kanR and antibiotic-free SV40 and PAS-BH backbones.

TABLE 2

Antibiotic-free vector expression and manufacture

| Construct | Size (kb) | ID† | Selection | Ferm Yield (mg/L) | Specific yield (mg/L/$OD_{600}$) | Ferm Spec Yield/size | Expression (HEK293) |
|---|---|---|---|---|---|---|---|
| gWIZ-EGFP | 5.75 | RF193 | Kan | 1370 | 16.25 | 2.8 | 38,190 ± 9,329 |
| NTC7482-41H-HA | 6.21 | RF205 | Kan | 2200 | 24.9 | 4.0 | ND |
| NTC8385[b] | 3.59 | RF247 | Sucrose | 775 | 9.11 | 2.5 | 47,808 ± 12,916[a] |
| NTC8485[b] | 3.80 | RF248 | Sucrose | 1210 | 16.2 | 4.4 | 52,141 ± 7,356[a] |
| NTC8685[b] | 3.68 | RF252 | Sucrose | 1055 | 12.7 | 3.5 | 60,418 ± 2,624[a] |

†All fermentations induced at 50 $OD_{600}$ for 10.5 h at 42° C., 1 h 25° C. hold
[a]Expression from equivalent EGFP-encoding vector
[b]NTC8385 and NTC8485 vector backbones were modified to contain the identical VA RNAI regulatory RNA as is present in NTC8685. All three vectors encode the same 585 bp transgene.

In summary, the novel SV40 enhancer and PAS-BH vector modifications resulted in dramatically higher increases in fermentation yields than previously defined yield improving modifications such as optimizing the orientation of the kanR and replication origin (Williams, Supra, 2006) or reduction of kanR gene expression (pLL14; Audonnet, J. 2008 World Patent Application WO2008136790). Indeed, the modifications do not require a kanR gene to improve copy number, and improved copy number was observed with the RNA-OUT RNA-based selectable marker as well. These modifications should therefore also improve plasmid copy number with a wide variety of alternative selection markers.

Example 5

NTC8682, NTC8482, NTC7682, NTC7482, NTC8685, NTC8485, NTC7685, and NTC7485 Vectors A series of kanR and AF eukaryotic expression vectors incorporating the novel SV40 enhancer and PAS-BH vector modifications were made. The features of these vectors (NTC8682, NTC8482, NTC7682, NTC7482, NTC8685, NTC8485, NTC7685, and NTC7485) are summarized in Table 3.

NTC8682, NTC8482, NTC8685, and NTC8485 are antibiotic-free RNA-OUT versions of the kanR NTC7682, NTC7482, NTC7685, and NTC7485 equivalents.

NTC8482, NTC8485, NTC7482 and NTC7485 contain the full SV40-CMV enhancer region (FIG. 3) while NTC8682, NTC8685, NTC7682 and NTC7685 all contain the CMV upstream region deletion between the SV40 enhancer and the CMV enhancer (FIG. 3).

NTC8682, NTC8685, NTC7682 and NTC7685 additionally contain the expression enhancing Adenoviral serotype 5 VA RNAI regulatory RNA (VA1; FIG. 2) while NTC8482, NTC8485, NTC7482 and NTC7485 do not.

NTC8482, NTC7682, NTC7482 and NTC8682 all express the secreted transgene product as TPA fusion proteins while, NTC8685, NTC8485, NTC7485 and NTC7685 all express the native transgene product from a vector encoded ATG start codon.

The remainder of the vector sequences is identical between the different vectors.

These are just a few possible nonlimiting vector configurations. Many alternative vector configurations incorporating the novel SV40 enhancer and PAS-BH vector modifications may also be made, including but not limited to vectors with alternative selection markers, alternative promoters, alternative terminators, and different orientations of the various vector-encoded elements.

sequence (SEQ ID NO:14). The WA ATG start codon is double underlined and the SalI site single underlined.

```
SEQ ID NO: 14:
atggatgcaatgaagagagggctctgctgtgtgctgctgctgtgtggagcagt
cttcgtttcgcccagcggtaccggatccgtcgac
```

For precise cloning, genes are copied by PCR amplification from clones, cDNA, or genomic DNA using primers with SalI (5' end) and BglII (3' end) sites. Alternatively, genes are synthesized chemically to be compatible with the unique SalI/BglII cloning sites in these vectors.

For NTC8685, NTC8485, NTC7685, and NTC7485, the start codon ATG must immediately follow the SalI site (GTCGACATG). For NTC8682, NTC8482, NTC7682, and NTC7482, the ATG is optional but the same reading frame must be retained. For all vectors one or two stop codon (preferably TAA or TGA) must be included prior to the BglII site. A PCR product designed for NTC8685, NTC8485, NTC7685, and NTC7485 vectors is compatible with, and can also be cloned into, the NTC8682, NTC8482, NTC7682, and NTC7482 vectors.

Thus, the reader will see that the improved copy number vectors of the invention provide for a rational approach to improve production yield of plasmids.

While the basis for yield improvement is unknown, optimal vectors are expected to have a higher copy number due to reduction of replication inhibiting factors and incorporation of replication promoting factors. Completion of replication can be confounded by many factors, including: sequences that cause inhibition of DNA polymerase III replication [such as protein-DNA complexes assembled on replication termini (Ter) or repressor binding sequences; stable RNA-DNA hybrids]; unusual DNA structures [e.g. internal-ribosome entry sites; Levy J. 2003 US Patent Application US2003180949]; or head on transcription-replication collisions. As well, yield may be improved by replication promoting factors that increase RNA primer synthesis rate and/or

TABLE 3

NTC8682, NTC8482, NTC7682, NTC7482, NTC8685, NTC8485, NTC7685, and NTC7485 vectors

| Vector | Selection | VA RNAI present | Upstream region deletion | Transgene targeting |
|---|---|---|---|---|
| NTC8682 (SEQ ID NO: 8) | Sucrose | Yes | Yes | Secretion (TPA) |
| NTC8482 (SEQ ID NO: 9) | Sucrose | No | No | Secretion (TPA) |
| NTC7682 (SEQ ID NO: 12) | Kanamycin | Yes | Yes | Secretion (TPA) |
| NTC7482 (SEQ ID NO: 13) | Kanamycin | No | No | Secretion (TPA) |
| NTC8685 (SEQ ID NO: 6) | Sucrose | Yes | Yes | Native |
| NTC8485 (SEQ ID NO: 7) | Sucrose | No | No | Native |
| NTC7685 (SEQ ID NO: 10) | Kanamycin | Yes | Yes | Native |
| NTC7485 (SEQ ID NO: 11) | Kanamycin | No | No | Native |

An example strategy for cloning into these vectors is outlined below.

```
GTCGACATG--------Gene of interest----Stop codon------AGATCT
SalI                                                  BglII
```

For the NTC8685, NTC8485, NTC7685, and NTC7485 vectors, the ATG start codon (double underlined) is immediately preceded by a unique SalI site. The SalI site is an effective Kozak sequence for translational initiation. In NTC8682, NTC8482, NTC7682, and NTC7482, the SalI site is downstream in frame with the optimized TPA secretion replication primer utilization. For example, optimization of the orientation of the selectable marker relative to the replication origin (Williams, Supra, 2006) or reducing the strength of the selectable marker promoter (Audonnet, Supra, 2008) may reduce marker mediated transcriptional interference of replication primer synthesis and/or reduce head on transcription-replication collisions. While not limiting the application of the invention, inclusion of a primosomal assembly site such as PAS-BH may be beneficial at a later replication step, through increasing the percent of replication primers that successfully initiate DNA polymerase III mediated replication cycles.

While the above description contains many examples, these should not be construed as limitations on the scope of the invention, but rather should be viewed as an exemplification of preferred embodiments thereof. Many other variations are possible. For example, the selectable marker may be substituted with an alternative selectable marker. Likewise, the vectors may contain alternative promoters, terminators and/or transgenes to the examples provided herein. The orientation of the various vector-encoded elements may be changed relative to each other. The vectors may optionally contain additional functionalities, such as nuclear localizing sequences, the adenoviral VA RNAI, and/or immunostimulatory RNA elements as disclosed in Williams, Supra, 2008. Vectors containing combinations of SV40 enhancers and/or primosomal assembly sites could be rapidly created and screened for improved copy number. Alternatively, one or more primosomal assembly sites and/or SV40 enhancers could be inserted into different regions of a vector, in different orientations, and the resultant vectors screened for improved copy number. Alternatively, plasmid copy number may be improved by deletion of transcriptional terminators in existing vectors.

Accordingly, the scope of the invention should be determined not by the embodiments illustrated, but by the appended claims.

```
SEQ ID NO: 1: pNTCUltra1 PAS-BH (6826 bp)
cgggcttttttttcttaggctgcctcgcgcgtttcggtgatgacggtgaa aacctctgacacatgcagctcccggagacggtcacagcttgtctgtaagc ggatgccgggagcagacaagcccgtcagggcgcgtcagcgggtgttggcg ggtgtcgggcgcagccatgacccagtcacgtagcgatagcggagtgtat actggcttaactatgcggcatcagagcagattgtactgagagtgcaccat atgcggtgtgaaataccgcacagatgcgtaaggagaaaataccgcatcag gcgctcttccgcttcctcgctcactgactcgctgcgctcggtcgttcggc tgcggcgagcggtatcagctcactcaaaggcggtaatacggttatccaca gaatcaggggataacgcaggaaagaacatgtgagcaaaaggccagcaaaa ggccaggaaccgtaaaaaggccgcgttgctggcgtttttccataggctcc gcccccctgacgagcatcacaaaaatcgacgctcaagtcagaggtggcaa acccgacaggactataaagataccaggcgtttccccctggaagctccctc gtgcgctctcctgttccgaccctgccgcttaccggatacctgtccgcctt tctcccttcgggaagcgtggcgctttctcatagctcacgctgtaggtatc tcagttcggtgtaggtcgttcgctccaagctgggctgtgtgcacgaaccc cccgttcagcccgaccgctgcgccttatccggtaactatcgtcttgagtc caacccggtaagacacgacttatcgccactggcagcagccactggtaaca ggattagcagagcgaggtatgtaggcggtgctacagagttcttgaagtag tggcccctactacggctacactagaagaacagtatttggtatctgcgctct gctgaagccagttaccttcggaaaaagagttggtagctcttgatccggca aacaaaccaccgctggtagcggtggttttttttgtttgcaagcagcagatt acgcgcagaaaaaaggatctcaagaagatcctttgatcttttctacggg gtctgacgctcagtggaacgaaaactcacgttaagggattttggtcatga gattatcaaaaggatcttcacctagatccttttaaattaaaaatgaagt tttaaatcaatctaaagtatatatgagtaaacttggtctgacagttacca atgcttaatcagtgaggcacctatctcagcgatctgtctatttcgttcat ccatagttgcctgactcctgcaaaccacgttgtgtctcaaaatctctgat gttacattgcacaagataaaatatatcatcatgaacaataaaactgtctg cttacataaacagtaatacaaggggtgttatgagccatattcaacgggaa acgtcttgctcgaggccgcgattaaattccaacatggatgctgatttata tgggtataaatgggctcgcgataatgtcgggcaatcaggtgcgacaatct atcgattgtatgggaagcccgatgcgccagagttgtttctgaaacatggc aaaggtagcgttgccaatgatgttacagatgagatggtcagactaaactg gctgacggaatttatgcctcttccgaccatcaagcattttatccgactcc tgatgatgcatggttactcaccactgcgatccccgggaaaacagcattcc aggtattagaagaatatcctgattcaggtgaaaatattgttgatgcgctg gcagtgttcctgcgccggttgcattcgattcctgtttgtaattgtcctttt taacagcgatcgcgtatttcgtctcgctcaggcgcaatcacgaatgaata acggtttggttgatgcgagtgattttgatgacgagcgtaatggctggcct gttgaacaagtctggaaagaaatgcataagcttttgccattctcaccgga ttcagtcgtcactcatggtgatttctcacttgaaaccttattttttgacga ggggaaattaataggttgtattgatgttggacgagtcggaatcgcagacc gataccaggatcttgccatcctatggaactgcctcggtgagttttctcct tcattacagaaacggctttttcaaaaatatggtattgataatcctgatat gaataaattgcagtttcatttgatgctcgatgagttttttctaagccctga tcactgtggaatgtgtgtcagttagggtgtggaaagtccccaggctcccc agcaggcagaagtatgcaaagcatgcatctcaattagtcagcaaccaggt gtggaaagtccccaggctccccagcaggcagaagtatgcaaagcatgcat ctcaattagtcagcaaccatagtcccgcccctaactccgcccatcccgcc cctaactccgcccaggatccgctctagatggccattgcatacgttgtatc catatcataatatgtacatttatattggctcatgtccaacattaccgcca tgttgacattgattattgactagttattaatagtaatcaattacggggtc attagttcatagcccatatatggagttccgcgttacataacttacggtaa atggcccgcctggctgaccgcccaacgacccccgcccattgacgtcaata atgacgtatgttcccatagtaacgccaatagggactttccattgacgtca atgggtggagtatttacggtaaactgcccacttggcagtacatcaagtgt atcatatgccaagtacgccccctattgacgtcaatgacggtaaatggccc gcctggcattatgcccagtacatgaccttatgggactttcctacttggca gtacatctacgtattagtcatcgctattaccatggtgatgcggttttggc agtacatcaatgggcgtggatagcggtttgactcacggggatttccaagt ctccacccattgacgtcaatgggagtttgttttggcaccaaaatcaacg ggactttccaaaatgtcgtaacaactccgccccattgacgcaaatgggcg
```

-continued gtaggcgtgtacggtggggaggtctatataagcagagctcgtttagtgaac cgtcagacacttgctaaagacaataacaaatttacttgcaatcccccaaa acagacaggtaagtatcctttttacagcacaacttaatgagacagataga aactggtcttgtagaaacagagagtcgcctgcttttctgccaggtgctga cttctctcccctgggcttttcttttctcaggttgaaaagaagaagacg aagaagacgaagaagacaaagccgccaccatgcagatcttcgtgaagacc ctgacgggcaagaccaccactcttggggtcgagcccagtgacaccatcga gaatgtcaaggccaagatccaagacaaggaaggcatcccacctgaccagc agaggctgatattcgcgggcaaacagctggaggatggccgcaccctgtcc gactacaacatccagaaagagtccaccttgcacctggtgctgcgtctgcg cggtgccgctatggaggtgaagcaggagaaccggctgctcaacgaaagcg aaagcagcagccagggcctgctcggctactacttcagcgacctgaacttc caggctcccatggtggtgaccagcagcaccaccggcgatctgagcatccc cagcagcgagctggagaacatccccagcgagaaccagtacttccagagcg ccatctggagcggcttcatcaaggtgaagaaaagcgatgagtacaccttc gctaccagcgctgacaaccacgtgaccatgtgggtggacgatcaggaagt gatcaacaaggccagcaacagcaacaaaatccggctggagaagggccggc tgtaccagatcaagatccagtaccagcgggaaaaccccaccgagaagggc ctggacttcaagctgtactggaccgacagccagaacaagaaagaagtgat cagcagcgataacctgcagctgcccgagctgaagcagaagagcagcaaca gccggaaaaaacggagcaccagcgctggccccaccgtgcccgatcgggat aacgatggcatccccgatagcctggaagtggagggctacaccgtggacgt gaagaacaaacggaccttcctgagcccctggatcagcaacatccacgaga agaaaggcctgaccaagtacaaaagcagccccgaaaaatggagcaccgct agcgaccccacagcgatttcgagaaggtgaccggccggatcgacaaaaa cgtgagccccgaagctcggcacccccctggtggctgcttaccccatcgtgc acgtggacatggagaacatcatcctgagcaagaacgaagatcagagcacc cagaacaccgacagcgagacccggaccatcagcaaaaacaccagcaccag ccggacccacaccagcgaagtgcacgcaacgccgaggtgcacgctagct tcttcgatatcggcggcagcgtgagcgctggcttcagcaacagcaacagc agcaccgtggctatcgatcacagcctgagcctggctggcgaacggacctg ggctgaaaccatgggcctgaacaccgctgataccgctcggctgaacgcta acatccggtacgtgaacaccggcaccgctcccatctacaacgtgctgccc accaccagcctggtgctgggcaagaaccagaccctggccaccatcaaggc caaggaaaaaccagctgagccagatcctggcccccaacaactactacccca gcaaaaacctggctcccatcgctctgaacgctcaggacgatttcagcagc accccccatcaccatgaactacaaccagttcctggagctggagaagaccaa acagctgcggctggataccgaccaggtgtacggcaacatcgccacctaca acttcgaaaacggccgggtgcgggtggataccggcagcaactggagcgaa gtgctgccccagatccaggaaaccaccgcccggatcatcttcaacggcaa ggatctgaacctggtggaacggcggatcgctgctgtgaaccccagcgatc ccctggagaccaccaaacccgacatgaccctgaaggaggccctgaagatc gccttcggcttcaacgaacccaacggcaacctgcagtaccagggcaagga catcaccgagttcgacttcaacttcgaccagcagaccagccagaacatca aaaaccagctggccgagctgaacgccaccaacatctacaccgtgctggac aagatcaagctgaacgccaagatgaacatcctgatccgggacaagcgttc cactacgatcggaacaacatcgctgtgggcgctgatgaaagcgtggtgaa ggaagctcaccgggaagtgatcaacagcagcaccgagggcctgctcctga acatcgacaaggacatccggaagatcctgagcggctacatcgtggagatc gaggacaccgagggcctgaaggaagtgatcaacgaccggtacgacatgct gaacatcagcagcctgcggcaggacggcaagaccttcatcgacttcaaga atacaacgacaagctgcccctgtacatcagcaaccccaactacaaggtg aacgtgtacgccgtgaccaaggagaacaccatcatcaaccccagcgaaaa cggcgacaccagcaccaacggcatcaagaaaatcctgatcttcagcaaga aaggctacgagatcggcggcccggtcgccaccatggtgagcaagggcgag gagctgttcaccggggtggtgcccatcctggtcgagctggacggcgacgt aaacggccacaagttcagcgtgtccggcgagggcgagggcgatgccacct acggcaagctgaccctgaagttcatctgcaccaccggcaagctgcccgtg ccctggcccaccctcgtgaccaccctgacctacggcgtgcagtgcttcag ccgctaccccgaccacatgaagcagcacgacttcttcaagtccgccatgc ccgaaggctacgtccaggagcgcaccatcttcttcaaggacgacggcaac tacaagacccgcgccgaggtgaagttcgagggcgacaccctggtgaaccg catcgagctgaagggcatcgacttcaaggaggacggcaacatcctgggc acaagctggagtacaactacaacagccacaacgtctatatcatggccgac aagcagaagaacggcatcaaggtgaacttcaagatccgccacaacatcga ggacggcagcgtgcagctcgccgaccactaccagcagaacacccccatcg gcgacggccccgtgctgctgcccgacaaccactacctgagcacccagtcc gccctgagcaaagaccccaacgagaagcgcgatcacatggtcctgctgga gttcgtgaccgccgccgggatcactctcggcatggacgagctgtacaagt aactcgagccgcagatctttttccctctgccaaaaattatggggacatca tgaagcccttgagcatctgacttctggctaataaaggaaatttatttca ttgcaatagtgtgttggaattttttgtgtctctcactcggaaggacataa gggcggccgcaacgacgagaacgaacgaagaacgctcgagagtcgattta aatcccccctgtatcgatgcactgcctcgatgctgcatcgatgcacaaaa tgctagcccgcctaatgag SEQ ID NO: 2: SV40 enhancer (212 bp)
ctgtggaatgtgtgtcagttagggtgtggaaagtccccaggctccccagc aggcagaagtatgcaaagcatgcatctcaattagtcagcaaccaggtgtg gaaagtccccaggctccccagcaggcagaagtatgcaaagcatgcatctc aattagtcagcaaccatagtcccgcccctaactccgcccatcccgcccct aactccgcccag SEQ ID NO: 3: PAS-BH (48 bp)
cagctcccggagacggtcacagcttgtctgtaagcggatgccgggagc SEQ ID NO: 4: pBR322 origin region between ROP and
PAS-BL (pBR322 2067-2351) (285 bp)
ctgccctcgcgcgtttcggtgatgacggtgaaaacctctgacacatgcagc tcccggagacggtcacagcttgtctgtaagcggatgccgggagcagacaa gcccgtcagggcgcgtcagcgggtgttggcgggtgtcggggcgcagccat gacccagtcacgtagcgatagcggagtgtatactggcttaactatgcggc atcagagcagattgtactgagagtgcaccatatgcggtgtgaaataccgc acagatgcgtaaggagaanataccgcatcaggcgc SEQ ID NO: 5: ApaI-KpnI dual terminator (101 bp)
GGGCCCACCGATACAATTAAAGGCTCCTTTTGGAGCCTTTTTTTTGGAC

TGCAAACAAATAGTCAAAAGCCTCCGGTCGGAGGCTTTTGACTTTGGTAC

C

SEQ ID NO: 6: NTC8685 (3095 bp)
ccgcctaatgagcgggcttttttttcttaggctgcctcgcgcgtttcggtgatgacggtgaaaacctctgacacatgcagctcccggagacggtcacagcttgtctgtaagcggatgccgggagcagacaagcccgtcagggcgcgtcagcgggtgttggcgggtgtcggggcgcagccatgacccagtcacgagcga tagcggagtgtatactggcttaactatgcggcatcagagcagattgtact gagagtgcaccatatgcggtgtgaaataccgcacagatgcgtaaggagaa aataccgcatcaggcgctcttccgcttcctcgctcactgactcgctgcgc tcggtcgttcggctgcggcgagcggtatcagctcactcaaaggcggtaat acggttatccacagaatcagggggataacgcaggaaagaacatgtgagcaa aaggccagcaaaaggccaggaaccgtaaaaaggccgcgttgctggcgttt ttccataggctccgcccccctgacgagcatcacaaaaaatcgacgctcaa gtcagaggtggcgaaacccgacaggactataaagataccaggcgtttccc cctggaagctccctcgtgcgctctcctgttccgaccctgccgcttaccgg atacctgtccgcctttctcccttcgggaagcgtggcgctttctcatagct cacgctgtaggtatctcagttcggtgtaggtcgttcgctccaagctgggc tgtgtgcacgaaccccccgttcagcccgaccgctgcgccttatccggtaac tatcgtcttgagtccaacccgtaagacacgacttatcgccactggcagc agccactggtaacaggattagcagagcgaggtatgtaggcggtgctacag agttcttgaagtggtggcctaactacggctacactagaagaacagtattt ggtatctgcgctctgctgaagccagttaccttcggaaaaagagttggtag ctcttgatccggcaaacaaaccaccgctggtagcggtggtttttttgttt gcaagcagcagattacgcgcagaaaaaaggatctcaagaagatcctttga tcttttctacggggtctgacgctcagtggaacgaaaactcacgttaaggg attttggtcatgagattatcaaaaaggatcttcacctagatccttaaatt aaaaatgaagttttaaatcaatctaaagtatatatgagtaaacttggtct gacagttaccaatgcttaatcagtgaggcacctatctcagcgatctgtct atttcgttcatccatagttgcctgactccctgcaaaccacgttgtggtaga attggtaaagagagtcgtgtaaaatatcgagttcgcacatcttgttgtct gattattgattttggcgaaaccatttgatcatatgacaagatgtgtatc taccttaacttaatgattttgataaaaatcattaggtaccctgatcact gtggaatgtgtgtcagttagggtgtggaaagtccccaggctccccagcag gcagaagtatgcaaagcatgcatctcaattagtcagcaaccaggtgtgga aagtccccaggctccccagcaggcagaagtatgcaaagcatgcatctcaa ttagtcagcaaccatagtcccgcccctaactccgcccatcccgcccctaa ctccgcccagttacggggcattagttcatagcccatatatggagttccg cgttacaaacttacggtaaatggcccgcctggctgaccgcccaacgaccc ccgcccattgacgtcaataatgacgtatgttcccatagtaacgccaatag ggactttccattgacgtcaatgggtggagtatttacggtaaactgcccac ttggcagtacatcaagtgtatcatatgccaagtacgccccctattgacgt caatgacggtaaatggcccgcctggcattatgcccagtacatgaccttat gggactttcctacttggcagtacatctacgtattagtcatcgctattacc atggtgatgcggttttggcagtacatcaatgggcgtggatagcggtttga ctcacggggatttccaagtctccaccccattgacgtcaatgggagtttgt tttggcaccaaaatcaacgggactttccaaaatgtcgtaacaactccgcc ccattgacgcaaatgggcggtaggcgtgtacggtgggaggtctatataag cagagctcgtttagtgaaccgtcagatcgcctggagacgccatccacgct gttttgacctccatagaagacaccgggaccgatccagcctccgcggctcg catctctccttcacgcgcccgccgccctacctgaggccgccatccacgcc ggttgagtcgcgttctgccgcctcccgcctgtggtgcctcctgaactgcg tccgccgtctaggtaagtttaaagctcaggtcgagaccgggcctttgtcc ggcgctcccttggagcctacctagactcagccggctctccacgctttgcc tgaccctgcttgctcaactctagttctctcgttaacttaatgagacagat agaaactggtcttgtagaaacagagtagtcgcctgcttttctgccaggtg ctgacttctctccctgggctttttcttttttctcaggttgaaaagaaga agacgaagaagacgaagaagacaaaccgtcgtcgacagatctttttccct ctgccaaaaattatggggacatcatgaagcccttgagcatctgacttct ggctaataaaggaaatttattttcattgcaatagtgtgttggaattttttt gtgtctctcactcggaaggacataagggcggccgctagc SEQ ID NO: 7: NTC8485 (3016 bp)
ccgcctaatgagcgggcttttttttcttaggctgcctcgcgcgtttcggt gatgacggtgaaaacctctgacacatgcagctcccggagacggtcacagc ttgtctgtaagcggatgccgggagcagacaagcccgtcagggcgcgtcag cgggtgttggcgggtgtcggggcgcagccatgacccagtcacgtagcgat agcggagtgtatactggcttaactatgcggcatcagagcagattgtactg agagtgcaccatatgcggtgtgaaataccgcacagatgcgtaaggagaaa -continued ataccgcatcaggcgctcttccgcttcctcgctcactgactcgctgcgct
cggtcgttcggctgcggcgagcggtatcagctcactcaaaggcggtaata
cggttatccacagaatcaggggataacgcaggaaagaacatgtgagcaaa
aggccagcaaaaggccaggaaccgtaaaaaggccgcgttgctggcgtttt
tccataggctccgcccccctgacgagcatcacaaaaatcgacgctcaagt
cagaggtggcgaaacccgacaggactataaagataccaggcgtttccccc
tggaagctccctcgtgcgctctcctgttccgaccctgccgcttaccggat
acctgtccgcctttctcccttcgggaagcgtggcgctttctcatagctca
cgctgtaggtatctcagttcggtgtaggtcgttcgctccaagctgggctg
tgtgcacgaaccccccgttcagcccgaccgctgcgccttatccggtaaca
tcgtcttgagtccaacccggtaagacacgacttatcgccactggcagcag
ccactggtaacaggattagcagagcgaggtatgtaggcggtgctacagag
ttcttgaagtggtggcctaactacggctacactagaagaacagtatttgg
atctgcgctctgctgaagccagttaccttcggaaaaagagttggtagctc
ttgatccggcaaacaaaccaccgctggtagcggtggtttttttgtttgca
agcagcagattacgcgcagaaaaaaaggatctcaagaagatcctttgatc
ttttctacggggtctgacgctcagtggaacgaaaactcacgttaagggat
tttggtcatgagattatcaaaaaggatcttcacctagatccttttaaatt
aaaaatgaagttttaaatcaatctaaagtatatatgagtaaacttggtct
gacagttaccaatgcttaatcagtgaggcacctatctcagcgatctgtct
atttcgttcatccatagttgcctgactcctgcaaaccacgttgtggtaga
attggtaaagagagtcgtgtaaaatatcgagttcgcacatcttgttgtct
gattattgattttggcgaaaccatttgatcatatgacaagatgtgtatc
taccttaacttaatgattttgataaaaatcattaggtaccctgatcact
gtggaatgtgtgtcagttagggtgtggaaagtccccaggctccccagcag
gcagaagtatgcaaagcatgcatctcaattagtcagcaaccaggtgtgga
aagtccccaggctccccagcaggcagaagtatgcaaagcatgcatctcaa
ttagtcagcaaccatagtcccgcccctaactccgcccatcccgcccctaa
ctccgcccaggatccgctctagatggccattgcatacgttgtatccatat
cataatatgtacatttatattggctcatgtccaacattaccgccatgttg
acattgattattgactagttattaatagtaatcaattacggggtcattag
ttcatagcccatatatggagttccgcgttacataacttacggtaaatggc
ccgcctggctgaccgcccaacgaccccgcccattgacgtcaataatgac
gtatgttcccatagtaacgccaatagggactttccattgacgtcaatggg
tggagtatttacggtaaactgcccacttggcagtacatcaagtgtatcat
atgccaagtacgccccctattgacgtcaatgacggtaaatggcccgcctg
gcattatgcccagtacatgaccttatgggactttcctacttggcagtaca
tctacgtattagtcatcgctattaccatggtgatgcggttttggcagtac
atcaatgggcgtggatagcggtttgactcacggggatttccaagtctcca
ccccattgacgtcaatgggagtttgttttggcaccaaaatcaacgggact
ttccaaaatgtcgtaacaactccgccccattgacgcaaatgggcggtagg -continued cgtgtacggtgggaggtctatataagcagagctcgtttagtgaaccgtca
gatcgcctggagacgccatccacgctgttttgacctccatagaagacacc
gggaccgatccagcctccgcggctcgcatctctccttcacgcgcccgccg
ccctacctgaggccgccatccacgccggttgagtcgcgttctgccgcctc
ccgcctgtggtgcctcctgaactgcgtccgccgtctaggtaagtttaaag
ctcaggtcgagaccgggcctttgtccggcgctcccttggagcctacctag
actcagccggctctccacgctttgcctgaccctgcttgctcaactctagt
tctctcgttaacttaatgagacagatagaaactggtcttgtagaaacaga
gtagtcgcctgcttttctgccaggtgctgacttctctcccctgggctttt
ttcttttctcaggttgaaaagaagaagacgaagaagacgaagaagacaa
accgtcgtcgacagatcttttcccctctgccaaaattatggggacatcat
gaagccccttgagcatctgacttctggctaataaaggaaatttatttca
ttgcaatagtgtgttggaattttttgtgtctctcactcggaaggacataa
ggcggccgctagc SEQ ID NO: 8: NTC8682 (3186 bp)
ccgcctaatgagcgggcttttttttcttagggtgcaaaaggagagcctga
agcgggcactcttccgtggtctggtggataaattcgcaagggtatcatgg
cggacgaccggggttcgagccccgtatccggccgtccgccgtgatccatg
cggttaccgcccgcgtgtcgaacccaggtgtgcgacgtcagacaacgggg
gagtgctccttttggcttccttcccctaccggtctgcctcgcgcgtttcg
gtgatgacggtgaaaacctctgacacatgcagctcccggagacggtcaca
gcttgtctgtaagcggatgccgggagcagacaagcccgtcagggcgcgtc
agcgggtgttggcgggtgtcggggcgcagccatgacccagtcacgtagcg
atagcggagtgtatactggcttaactatgcggcatcagagcagattgtac
tgagagtgcaccatatgcggtgtgaaataccgcacagatgcgtaaggaga
aaataccgcatcaggcgctcttccgcttcctcgctcactgactcgctgcg
ctcggtcgttcggctgcggcgagcggtatcagctcactcaaaggcggtaa
tacggttatccacagaatcaggggataacgcaggaaagaacatgtgagca
aaaggccagcaaaaggccaggaaccgtaaaaaggccgcgttgctggcgttt
ttccataggctccgcccccctgacgagcatcacaaaaatcgacgctcaag
tcagaggtggcgaaacccgacaggactataaagataccaggcgtttcccc
ctggaagctccctcgtgcgctctcctgttccgaccctgccgcttaccgga
tacctgtccgcctttctcccttcgggaagcgtggcgctttctcatagctc
acgctgtaggtatctcagttcggtgtaggtcgttcgctccaagctgggct
gtgtgcacgaaccccccgttcagcccgaccgctgcgccttatccggtaac
tatcgtcttgagtccaacccggtaagacacgacttatcgccactggcagc
agccactggtacaggattagcagagcgaggtatgtaggcggtgctacaga
gttcttgaagtggtggcctaactacggctacactagaagaacagtatttg
gtatctgcgctctgctgaagccagttaccttcggaaaaagagttggtagc
tcttgatccggcaaacaaaccaccgctggtagcggtggtttttttgtttg
caagcagcagattacgcgcagaaaaaaaggatctcaagaagatcctttga tcttttctacggggtctgacgctcagtggaacgaaaactcacgttaaggg
attttggtcatgagattatcaaaaaggatcttcacctagatccttttaaa
ttaaaaatgaagttttaaatcaatctaaagtatatatgagtaaacttggt
ctgacagttaccaatgcttaatcagtgaggcacctatctcagcgatctgt
ctatttcgttcatccatagttgcctgactcctgcaaaccacgttgtggta
gaattggtaaagagagtcgtgtaaaatatcgagttcgcacatcttgttgt
ctgattattgattttggcgaaaccatttgatcatatgacaagatgtgta
tctaccttaacttaatgattttgataaaaatcattaggtaccccctgatca
ctgtggaatgtgtgtcagttagggtgtggaaagtccccaggctccccagc
aggcagaagtatgcaaagcatgcatctcaattagtcagcaaccaggtgtg
gaaagtccccaggctccccagcaggcagaagtatgcaaagcatgcatctc
aattagtcagcaaccatagtcccgcccctaactccgcccatcccgccct
aactccgcccagttacggggtcattagttcatagcccatatatggagttc
cgcgttacataaacttacggtaaatggcccgcctggctgaccgcccaacga
cccccgcccattgacgtcaataatgacgtatgttcccatagtaacgccaa
tagggacttcccattgacgtcaatgggtggagtatttacggtaactgccc
acttggcagacatcaatgtatcatatgccaagtacgccccctattgacgt
caatgacggtaaatggcccgcctggcattatgcccagacatgaccttatg
ggactttcctacttggcaggtacatctacgtattagtcatcgctattacc
atggtgatgcggttttggcagtacatcatgggcgtggatagcggtttgac
tcacggggatttccaagtctccaccccattgacgtcaatgggagtttgtt
ttggcaccaaaatcaacgggactttccaaaatgtcgtaacaactccgccc
cattgacgcaaatgggcggtaggcgtgtacggtgggaggtctatataagc
agagctcgtttagtgaaccgtcagatcgcctggagacgccatccacgctg
ttttgacctccatagaagacaccgggaccgatccagcctccgcggctcgc
atctctccttcacgcgcccgccgccctacctgaggccgccatccacgccg
gttgagtcgcgttctgccgcctcccgcctgtggtgcctcctgaactgcgt
ccgccgtctaggtaagtttaaagctcaggtcgagaccgggcctttgtccg
gcgctcccttggagcctacctagactcagccggctctccacgcttgcct
gaccctgcttgctcaactctagttctctcgttaactaatgagacagatag
aaaactggtcttgtagaaacagagtagtcgcctgcttttctgccaggtgct
gacttctctcccctgggcttttttctttttctcaggttgaaaagaagaag
acgaagaagacgaagaagacaaagccgccaccatggatgcaatgaagaga
gggctctgctgtgtgctgctgctgtgtggagcagtcttcgtttcgcccag
cggtaccggatccgtcgacgggggagatcttttccctctgccaaaaat
tatgggacatcatgaagcccttgagcatctgacttctggctaataaag
gaaatttattttcattgcaatagtgtgttggaatttttttgtgtctctcac
tcggaaggacataagggcggccgctagc SEQ ID NO: 9: NTC8482 (3107 bp)
ccgcctaatgagcgggcttttttttcttaggctgcctcgcgcgtttcggt
gatgacggtgaaaacctctgacacatgcagctcccggagacggtcacagc ttgtctgtaagcggatgccgggagcagacaagcccgtcagggcgcgtcag
cgggtgttggcgggtgtcggggcgcagccatgacccagtcacgtagcgat
agcggagtgtatactggcttaactatgcggcatcagagcagattgtactg
agagtgcaccatatgcggtgtgaaataccgcacagatgcgtaaggagaaa
ataccgcatcaggcgctcttccgcttcctcgctcactgactcgctgcgct
cggtcgttcggctgcggcgagcggtatcagctcactcaaaggcggtaata
cggttatccacagaatcaggggataacgcaggaaagaacatgtgagcaaa
aggccagcaaaaggccaggaaccgtaaaaaggccgcgttgctggcgtttt
tccataggctccgcccccctgacgagcatcacaaaaatcgacgctcaagt
cagaggtggcgaaacccgacaggactataaagataccaggcgtttccccc
tggaagctccctcgtgcgctctcctgttccgaccctgccgcttaccggat
acctgtccgcctttctcccttcgggaagcgtggcgctttctcatagctca
cgctgtaggtatctcagttcggtgtaggtcgttcgctccaagctgggctg
tgtgcacgaaccccccgttcagcccgaccgctgcgccttatccggtaact
atcgtcttgagtccaacccggtaagacacgacttatcgccactggcagca
gccactggtaacaggattagcagagcgaggtatgtaggcggtgctacaga
gttcttgaagtggtggcctaactacggctacactagaagaacagtatttg
gtatctgcgctctgctgaagccagttaccttcggaaaaagagttggtagc
tcttgatccggcaaacaaaccaccgctggtagcggtggtttttttgtttg
caagcagcagattacgcgcagaaaaaaaggatctcaagaagatcctttga
tctttctacggggtctgacgctcagtggaacgaaaactcacgttaaggg
attttggtcatgagattatcaaaaaggatcttcacctagatccttttaaa
ttaaaaatgattttaaatcaatctaaagtatatatgagtaaacttggtct
gacagttaccaatgcttaatcagtgaggcacctatctcagcgatctgtct
atttcgttcatccaagttgcctgactcctgcaaaccacgtttgtggtaga
attggtaaagagagtcgtgtaaaatatcgagttcgcacatcttgttgtct
gattattgattttggcgaaaccatttgatcatatgacaagatgtgtatc
taccttaacttaatgattttgataaaaatcattaggtaccccctgatcact
gtggaatgtgtgtcagttagggtgtggaaagtccccaggctccccagcag
gcagaagtatgcaaagcatgcatctcaattagtcagcaaccaggtgtgga
aagtccccaggctccccagcaggcagaagtatgcaaagcatgcatctcaa
ttagtcagcaaccatagtcccgcccctaactccgcccatcccgcccctaa
ctccgcccaggatccgctctagatggccattgcatacgttgtatccatat
cataatatgtacatttatattggctcatgtccaacattaccgccatgttg
acattgattattgactagttattaatagtaatcaattacggggtcattag
ttcatagcccatatatggagttccgcgttacataaacttacggtaaatggc
ccgcctggctgaccgcccaacgacccccgcccattgacgtcaataatgac
gtatgttcccatagtaacgccaatagggacttcccattgacgtcaatggg
tggagtatttacggtaaactgcccacttggcagtacatcaagtgtatcat
atgccaagtacgccccctattgacgtcaatgacggtaaatggcccgcctg -continued

```
gcattatgcccagtacatgaccttatgggactttcctacttggcagtaca
tctacgtattagtcatcgctattaccatggtgatgcggttttggcagtac
atcaatgggcgtggatagcggtttgactcacggggatttccaagtctcca
ccccattgacgtcaatgggagtttgttttggcaccaaaatcaacgggact
ttccaaaatgtcgtaacaactccgccccattgacgcaatgggcggtaggc
gtgtacggtggggggtctatataagcagagctcgtttagtgaaccgtcag
atcgcctggagacgccatccacgctgttttgacctccatagaagacaccg
ggaccgatccagctccgcggctcgcatctctccttcacgcgcccgccgc
cctacctgaggccgccatccacgccggttgagtcgcgttctgccgcctcc
cgcctgtggtgcctcctgaactgcgtccgccgtctaggtaagtttaaagc
tcaggtcgagaccgggcctttgtccggcgctcccttggagcctacctaga
ctcagccggctctccacgctttgcctgaccctgcttgctcaactctagtt
ctctcgttaacttaatgagacagatagaaactggtcttgtagaaacagag
tagtcgcctgcttttctgccaggtgctgacttctctcccctgggcttttt
tcttttttctcaggttgaaagaagaagacgaagaagacgaagaagacaaa
gccgccaccatggatgcaatgaagagagggctctgctgtgtgctgctgct
gtgtggagcagtcttcgtttcgcccagcggtaccggatccgtcgacgggg
ggagatcttttcccctctgccaaaaattatggggacatcatgaagcccct
tgagcatctgacttctggctaataaaggaaatttattttcattgcaatag
tgtgttggaattttttgtgtctctcactcggaaggacataaggcggccgc
tagc
```

SEQ ID NO: 10: NTC7685 (3863 bp)
```
ccgcctaatgagcgggcttttttttcttagggtgcaaaaggagagcctgt
aagcgggcactcttccgtggtctggtggtaaaattcgcaagggtatcatg
gcggacgaccgggggttcgagcccgtatccggccgtccgccgtgatccat
gcggttaccgccgcgtgtcgaacccaggtgtgcgacgtcagacaacggg
ggagtgctcctttttggcttccttcccctaccggtctgcctcgcgcgtttc
ggtgatgacggtgaaaacctctgacacatgcagctcccggagacggtcac
agcttgtctgtaagcggatgccgggagcagacaagcccgtcagggcgcgt
cagcgggtgttggcgggtgtcggggcgcagccatgacccagtcacgtagc
gatagcggagtgtatactggcttaactatgcggcatcagagcagattgta
ctgagagtgcaccatatgcggtgtgaaataccgcacagatgcgtaaggag
aaaataccgcatcaggcgctcttccgcttcctcgctcactgactcgctgc
gctcggtcgttcggctgcggcgagcggtatcagctcactcaaaggcggta
atacggttatccacagaatcaggggataacgcaggaaagaacatgtgagc
aaaaggccagcaaaaggccaggaaccgtaaaaaggccgcgttgctggcgt
ttttccataggctccgcccccctgacgagcatcacaaaaatcgacgctca
agtcagaggtggcgaaacccgacaggactataaagataccaggcgtttcc
ccctggaagctccctcgtgcgctctcctgttccgaccctgccgcttaccg
gatacctgtccgcctttctcccttcgggaagcgtggcgctttctcatagc
tcacgctgtaggtatctcagttcggtgtaggtcgttcgctccaagctggg
```

-continued

```
ctgtgtgcacgaaccccccgttcagcccgaccgctgcgccttatccggta
actatcgtcttgagtccaacccggtaagacacgacttatcgccactggca
gcagccactggtaacaggattagcagagcgaggtatgaggcggtgctaca
gagttcttgaagtggtggcctaactacggctacactagaagaacagtatt
tggtatctgcgctctgctgaagccagttaccttcggaaaaagagttggta
gctcttgatccggcaaacaaaccaccgctggtagcggtggtttttttgtt
tgcaagcagcagattacgcgcagaaaaaaaggatctcaagaagatccttt
gatcttttctacggggtctgacgctcagtggaacgaaaactcacgttaag
ggattttggtcatgagattatcaaaaaggatcttcacctagatccttttta
aattaaaaatgaagttttaaatcaatctaaagtatatatgagtaaacttg
gtctgacagttaccaatgcttaatcagtgaggcacctatctcagcgatct
gtctatttcgttcatccatagttgcctgactccctgcaaaccacgttgtgt
ctcaaaatctctgatgttacattgcacaagataaaaatatatcatcatga
acaataaaactgtctgcttacataaacagtaatacaaggggtgttatgag
ccatattcaacgggaaacgtcttgctcgaggccgcgattaaattccaaca
tggatgctgatttatatgggtataaatgggctcgcgataatgtcgggcaa
tcaggtgcgacaatctatcgattgtatgggaagcccgatgcgccagagtt
gtttctgaaacatggcaaaggtagcgttgccaatgatgttacagatgaga
tggtcagactaaactggctgacggaatttatgcctcttccgaccatcaag
cattttatccgtactcctgatgatgcatggttactcaccactgcgatccc
cgggaaaacagcattccaggtattagaagaatatcctgattcaggtgaaa
atattgttgatgcgctggcagtgttcctgcgccggttgcattcgattcct
gtttgtaattgtcctttttaacagcgatcgcgtatttcgtctcgctcaggc
gcaatcacgaatgaataacggtttggttgatgcgagtgattttgatgacg
agcgtaatggctggcctgttgaacaagtctggaaagaaatgcataagctt
ttgccattctcaccggattcagtcgtcactcatggtgatttctcacttga
taacctattttttgacgaggggaaattaataggttgtattgatgttggac
gagtcggaatcgcagaccgataccaggatcttgccatcctatggaactgc
ctcggtgagttttctccttcattacagaaacggcttttttcaaaaatatgg
tattgataatcctgatatgaataaattgcagtttcatttgatgctcgatg
agtttttctaaccctgatcactgtggaatgtgtgtcagttagggtgtgga
aagtccccaggctcccagcaggcagaagtatgcaaagcatgcatctcaa
ttagtcagcaaccaggtgtggaaagtccccaggctcccagcaggcagaa
gtatgcaaagcatgcatctcaattagtcagcaaccatagtcccgcccta
actccgcccatcccgcccctaactccgcccagttacggggtcattagttc
atagcccataatggagttccgcgttacataacttacggtaaatggcccgc
ctggctgaccgcccaacgacccccgcccattgacgtcaataatgacgtat
gttcccatagtaacgccaataggactttccattgacgtcaatgggtgga
gtatttacggtaaactgcccacttggcagtacatcaagtgtatcatatgc
caagtacgccccctattgacgtcaatgacggtaaatggcccgcctggcat
tatgcccagtacatgaccttatgggactttcctacttggcagtacatcta
``` cgtattagtcatcgctattaccatggtgatgcggttttggcagtacatca
atgggcgtggatagcggtttgactcacggggatttccaagtctccacccc
attgacgtcaatgggagtttgttttggcaccaaaatcaacgggactttcc
aaaatgtcgtaacaactccgcccattgacgcaaatgggcggtaggcgtg
tacggtgggaggtctatataagcagagctcgtttagtgaaccgtcagatc
gcctggagacgccatccacgctgttttgacctccatagaagacaccggga
ccgatccagcctccgcggctcgcatctctccttcacgcgcccgccgccct
acctgaggccgccatccacgccggttgagtcgcgttctgccgcctcccgc
ctgtggtgcctcctgaactgcgtccgccgtctaggtaagtttaaagctca
ggtcgagaccgggcctttgtccggcgctccctggagcctacctagactc
agccggctctccacgctttgcctgaccctgcttgctcaactctagttctc
tcgttaacttaatgagacagatagaaactggtcttgtagaaacagagtag
tcgcctgcttttctgccaggtgctgacttctctcccctgggcttttttct
ttttctcaggttgaaaagaagaagacgaagaagacgaagaagacaaaccg
tcgtcgacagatcttttttccctctgccaaaaattatggggacatcatgaa
gccccttgagcatctgacttctggctaataaaggaaatttattttcattg
caatagtgtgttggaatttttttgtgtctctcactcggaaggacataaggg
cggccgctagc SEQ ID NO: 11: NTC7485 (3784 bp)
ccgcctaatgagcgggcttttttttcttaggctgcctcgcgcgtttcggt
gatgacggtgaaaacctctgacacatgcagctcccggagacggtcacagc
ttgtctgtaagcggatgccgggagcagacaagcccgtcagggcgcgtcag
cgggtgttggcgggtgtcggggcgcagccatgacccagtcacgtagcgat
agcggagtgtatactggcttaactatgcggcatcagagcagattgtactg
agagtgcaccatatgcggtgtgaaataccgcacagatgcgtaaggagaaa
ataccgcatcaggcgctcttccgcttcctcgctcactgactcgctgcgct
cggtcgttcggctgcggcgagcggtatcagctcactcaaaggcggtaata
cggttatccacagaatcaggggataacgcaggaaagaacatgtgagcaaa
aggccagcaaaaggccaggaaccgtaaaaaggccgcgttgctggcgtttt
tccataggctccgcccccctgacgagcatcacaaaaatcgacgctcaagt
cagaggtggcgaaacccgacaggactataaagataccaggcgtttccccc
tggaagctccctcgtgcgctctcctgttccgaccctgccgcttaccggat
acctgtccgcctttctcccttcgggaagcgtggcgctttctcatagctca
cgctgtaggtatctcagttcggtgtaggtcgttcgctccaagctgggctg
tgtgcacgaaccccccgttcagcccgaccgctgcgccttatccggtaacta
tcgtcttgagtccaacccggaagacacgacttatcgccactggcagcagc
cactggtaacaggattagcagagcgaggtatgtaggcggtgctacagagtt
cttgatggtggcctaactacggctacactagaagaacagtatttggtatc
tgctctgctgaagccagttaccttcggaaaaagagttggtagctcttga
tccggcaaacaaaccaccgctggtagcggtggtttttttgttgcaagca
gcagattacgcgcagaaaaaaaggatctcaagaagatcctttgatctttt ctacggggtctgacgctcagtggaacgaaaactcacgttaagggattttg
gtcatgagattatcaaaaaggatcttcacctagatccttttaaattaaaa
atgaagttttaaatcaatctaaagtatatatgagtaaacttggtctgacag
ttaccaatgcttaatcagtgaggcacctatctcagcgatctgtctatttc
gttcatccatagttgcctgactcctgcaaaccacgttgtgtctcaaaatc
tctgatgttacattgcacaagataaaaatatatcatcatgaacaataaaa
ctgtctgcttacataaacagtaatacaaggggtgttatgagccatattca
acgggaaacgtcttgctctgaggccgcgattaaattccaacatggatgctg
atttatatgggtataaatgggctcgcgataatgtcgggcaatcaggtgcg
acaatctatcgattgtatgggaagcccgatgcgccagagttgtttctgaa
acatggcaaaggtagcgttgccaatgatgttacagatgagatggtcagac
taaactggctgacggaatttatgcctcttccgaccatcaagcatttatc
cgtactcctgatgatgcatggttactcaccactgcgatccccgggaaaac
agcattccaggtattagagaatatcctgattcaggtgaaaatattgttga
tgcgctggcattcctgcgccggttgcattcgattcctgtttgtaattgtc
ctttttaacagcgatcgcgtatttcgtctcgctcaggcgcaatcacgaatg
aataacggtttggttgatgcgagtgattttgatgacgagcgtaatggctg
gcctgttgaacaagtctgaaagaaatgcataagcttttgccattctcac
cggattcagtcgtcactcatggtgatttctcacttgataaccttattttt
gacgaggggaaattaataggttgtattgatgttggacgagtcggaatcgc
agaccgataccaggatcttgccatcctatggaactgcctcggtgagtttt
ctccttcattacagaaacggctttttcaaaaatatggtattgataatcct
gatatgaataaaattgcagtttcatttgatgctcgatgagttttttctaacc
ctgatcactgtggaatgtgtgtcagttagggtgtggaaagtccccaggct
ccccagcaggcagaagtatgcaaagcatgcatctcaattagtcagcaacc
aggtgtggaaagtccccaggctccccagcaggcagaagtatgcaaagcat
gcatctcaattagtcagcaaccatagtcccgcccctaactccgcccatcc
cgcccctaactccgcccaggatccgctctagatggccattgcatacgttg
tatccatatcataatatgtacatttatattggctcatgtccaacattacc
gccatgttgacattgattattgactagttattaatagtaatcaattacgg
ggtcattagttcatagcccatatatggagttccgcgttacataacttacg
gtaaatggcccgcctggctgaccgcccaacgacccccgcccattgacgtc
aataatgacgtatgttcccatagtaacgccaatagggactttccattgac
gtcaatgggtggagtatttacggtaaactgcccacttggcagtacatcaa
gtgtatcatatgccaagtacgccccctattgacgtcaatgacggtaaatg
gcccgcctggcattatgcccagtacatgaccttatgggactttcctactt
ggcagtacatctacgtattagtcatcgctattaccatggtgatgcggttt
tggcagtacatcaatgggcgtggatagcggtttgactcacggggatttcc
aagtctccaccccattgacgtcaatgggagtttgttttggcaccaaaatc
aacgggactttccaaaatgtcgtaacaactccgcccattgacgcaaatg

```
ggcggtaggcgtgtacggtgggaggtctatataagcagagctcgtttagt
gaaccgtcagatcgcctggagacgccatccacgctgttttgacctccata
gaagacaccgggaccgatccagcctccgcggctcgcatctctccttcacg
cgcccgccgccctacctgaggccgccatccacgccggttgagtcgcgttc
tgccgcctcccgcctgtggtgcctcctgaactgcgtccgccgtctaggta
agtttaaagctcaggtcgagaccgggcctttgtccggcgctcccttggag
cctacctagactcagccggctctccacgctttgcctgaccctgcttgctc
aactctagttctctcgttaacttaatgagacagatagaaactggtcttgt
agaaacagagtagtcgcctgcttttctgccaggtgctgacttctctcccc
tgggcttttttcttttttctcaggttgaaaagaagaagacgaagaagacga
agaagacaaaccgtcgtcgacagatcttttttccctctgccaaaaattatg
gggacatcatgaagccccttgagcatctgacttctggctaataaaggaaa
tttattttcattgcaatagtgtgttggaattttttgtgtctctcactcgg
aaggacataaggcggccgctagc
SEQ ID NO: 12: NTC7682 (3954 bp)
ccgcctaatgagcgggcttttttttcttagggtgcaaaaggagagcctgt
aagcgggcactcttccgtggtctggtggtaaaattcgcaagggtatcatg
gcggacgaccggggttcgagcccgtatccggccgtccgccgtgatccat
gcggttaccgccgcgtgtcgaacccaggtgtgcgacgtcagacaacggg
ggagtgctccttttggcttccttcccctaccggtctgcctcgcgcgtttc
ggtgatgacggtgaaaacctctgacacatgcagctcccggagacggtcac
agcttgtctgtaagcggatgccggggagcagacaagcccgtcagggcgcgt
cagcgggtgttggcgggtgtcggggcgcagccatgacccagtcacgtagc
gatagcggagtgtatactggcttaactatgcggcatcagagcagattgta
ctgagagtgcaccatatgcggtgtgaaataccgcacagatgcgtaaggag
aaaataccgcatcaggcgctcttccgcttcctcgctcactgactcgctgc
gctcggtcgttcggctgcggcgagcggtatcagctcactcaaaggcggta
atacggttatccacagaatcaggggataacgcaggaaagaacatgtgagc
aaaaggccagcaaaaggccaggaaccgtaaaaaggccgcgttgctggcgt
ttttccataggctccgcccccctgacgagcatcacaaaaatcgacgctca
agtcagaggtggcgaaacccgacaggactataaagataccaggcgtttcc
ccctggaagctccctcgtgcgctctcctgttccgaccctgccgcttaccg
gatacctgtccgcctttctcccttcgggaagcgtggcgctttctcaagct
cacgctgtaggtatctcagttcggtgtaggtcgttcgctccaagctgggc
tgtgtgcacgaaccccccgttcagcccgaccgctgcgccttatccggtaa
ctatcgtcttgagtccaacccggtaagacacgacttatcgccactggcag
cagccactggtaacaggattagcagagcgaggtatgtaggcggtgctaca
gagttcttgaagtggtggcctaactacggctacactagaagaacagtatt
tggtatctgcgctctgctgaagccagttaccttcggaaaaagagttggta
gctcttgatccggcaaacaaaccaccgctggtagcggtggtttttttgtt
tgcaagcagcagattacgcgcagaaaaaaaggatctcaagaagatccttt
gatcttttctacggggtctgacgctcagtggaacgaaaactcacgttaag
ggattttggtcatgagattatcaaaaaggatcttcacctagatccttta
aattaaaaatgaagtttaaatcaatctaaagtatatatgagtaaacttgg
tctgacagttaccaatgcttaatcagtgaggcacctatctcagcgatctg
tctatttcgttcatccatagttgcctgactccctgcaaaccacgttgtgtc
tcaaaatctctgatgttacattgcacaagataaaaatatatcatcatgaa
caataaaactgtctgcttacataaacagtaatacaagggggtgttatgagc
catattcaacgggaaacgtcttgctcgaggccgcgattaaattccaacat
ggatgctgatttatatgggtataaatgggctcgcgataatgtcgggcaat
caggtgcgacaatctatcgattgtatgggaagcccgatgcgccagagttg
tttctgaaacatgcaaaggtagcgttgccaatgatgttacagatgagat
ggtcagactaaactggctgacggaatttatgcctcttccgaccatcaagc
attttatccgtactcctgatgatgcatggttactcaccactgcgatcccc
gggaaaacagcattccaggtattagaagaatatcctgattcaggtgaaaa
tattgttgatgcgctggcagtgttcctgcgccggttgcattcgattcctg
tttgtaattgtccttttaacagcgatcgcgtatttcgtctcgctcaggcg
caatcacgaatgaataacggtttggttgatgcgagtgattttgatgacga
gcgtaatggctggcctgttgaacaagtctggaaagaaatgcataagcttt
tgccattctcaccggattcagtcgtcactcatggtgatttctcacttgat
aaccttattttgacgaggggaaattaataggttgtattgatgttggacg
agtcggaatcgcagaccgataccaggatcttgccatcctatggaactgcc
tcggtgagttttctccttcattacagaaacggctttttcaaaaatatggt
attgataatcctgatatgaataaaattgcagtttcatttgatgctcgatga
gttttctaaccctgatcactgtggaatgtgtgtcagttagggtgtggaa
agtccccaggctccccagcaggcagaagtatgcaaagcatgcatctcaat
tagtcagcaaccaggtgtggaaagtccccaggctccccagcaggcagaag
tatgcaaagcatgcatctcaattagtcagcaaccatagtcccgcccctaa
ctccgcccatcccgcccctaactccgcccagttacggggtcattagttca
tagcccatatgaagttccgcgttacataacttacggtaaatggcccgcct
ggctgaccgcccaacgacccccgcccattgacgtcaataatgacgtatgt
tcccatagtaacgccaatagggactttccattgacgtcaatgggtggagt
atttacggtaaactgcccacttggcagtacatcaagtgtatcatatgcca
agtacgccccctattgacgtcaatgacggtaaatggcccgcctggcatta
tgcccagtacatgaccttatgggactttcctacttggcagtacatctacg
tattagtcatcgctattaccatggtgatgcggttttggcagtacatcaat
gggcgtggatagcggtttgactcacggggatttccaagtctccaccccat
tgacgtcatgggagtttgttttggcaccaaaatcaacgggactttccaaa
atgtcgtaacaactccgccccattgacgcaaatgggcggtaggcgtgtac
ggtgggaggtctatataagcagagctcgtttagtgaaccgtcagatcgcc
tggagacgccatccacgctgttttgacctccatagaagacaccgggaccg
atccagcctccgcggctcgcatctctccttcacgcgcccgccgccctacc
``` tgaggccgccatccacgccggttgagtcgcgttctgccgcctcccgcctg
tggtgcctcctgaactgcgtccgccgtctaggtaagtttaaagctcaggt
cgagaccgggcctttgtccggcgctcccttggagcctacctagactcagc
cggctctccacgctttgcctgaccctgcttgctcaactctagttctctcg
ttaacttaatgagacagatagaaactggtcttgtagaaacagagtagtcg
cctgcttttctgccaggtgctgacttctctccccctgggcttttttctttt
tctcaggttgaaaagaagaagacgaagaagacgaagaagacaaagccgcc
accatggatgcaatgaagagagggctctgctgtgtgctgctgctgtgtgg
agcagtcttcgtttcgcccagcggtaccggatccgtcgacggggggagat
cttttttccctctgccaaaaattatggggacatcatgaagcccttgagca
tctgacttctggctaataaaggaaatttattttcattgcaatagtgtgtt
ggaattttttgtgtctctcactcggaaggacataagggcggccgctagc
SEQ ID NO: 13: NTC7482 (3876 bp)
ccgcctaatgagcgggcttttttttcttaggctgcctcgcgcgtttcggt
gatgacggtgaaaacctctgacacatgcagctcccggagacggtcacagc
ttgtctgtaagcggatgccgggagcagacaagcccgtcagggcgcgtcag
cgggtgttggcgggtgtcggggcgcagccatgacccagtcacgtagcgat
agcggagtgtaactggcttaactatgcggcatcagagcagattgtactga
gagtgcaccatatgcggtgtgaaataccgcacagatgcgtaaggagaaaa
taccgcatcaggcgctcttccgcttcctcgctcactgactcgctgcgctc
ggtcgttcggctgcggcgagcggtatcagctcactcaaaggcggtaatac
ggttatccacagaatcaggggataacgcaggaaagaacatgtgagcaaaa
ggccagcaaaaggccaggaaccgtaaaaaggccgcgttgctggcgtttttc
cataggctccgcccccctgacgagcatcacaaaaatcgacgctcaagtca
gaggtggcgaaacccgacaggactataaagataccaggcgtttccccctg
gaagctccctcgtgcgctctcctgttccgaccctgccgcttaccggatac
ctgtccgcctttctcccttcgggaagcgtggcgctttctcatagctcacg
ctgtaggtatctcagttcggtgtaggtcgttcgctccaagctgggctgtg
tgcacgaaccccccgttcagcccgaccgctgcgccttatccggtaactat
cgtcttgagtccaacccggtaagacacgacttatcgccactggcagcagc
cactggtaacaggattagcagagcgaggtatgtaggcggtgctacagagt
tcttgaagtggtggcctaactacggctacactagaagaacagtatttggt
atctgcgctctgctgaagccagttaccttcggaaaaagagttggtagctc
ttgatccggcaaacaaaccaccgctggtagcggtggtttttttgtttgca
agcagcagattacgcgcagaaaaaaaggatctcaagaagatcctttgatc
ttttctacggggtctgacgctcagtggaacgaaaactcacgttaagggat
tttggtcatgagattatcaaaaaggatcttcacctagatccttttaaatt
aaaaatgaagttttaaatcaatctaaagtatatatgagtaaacttggtct
gacagttaccaatgcttaatcagtgaggcacctatctcagcgatctgtct
atttcgttcatccatagttgcctgactccctgcaaaccacgttgtctcaaa
atctctgatgttacattgcacaagataaaaatatatcatcatgaacaata
aaactgtctgcttacataaacagtaatacaagggggtgttatgagccatat
tcaacgggaaacgtcttgctcgaggccgcgattaaattccaacatggatg
ctgatttatatgggtataaatgggctcgcgataatgtcgggcaatcaggt
gcgacaatctatcgattgtatgggaagcccgatgcgccagagttgtttct
gaaacatggcaaaggtagcgttgccaatgatgttacagatgagatggtca
gactaaactggctgacggaatttatgcctcttccgaccatcaagcatttt
atccgtactcctgatgatgcatggttactcaccactgcgatccccgggaa
aacagcattccaggtattagaagaatatcctgattcaggtgaaaatattg
ttgatgcgctggcagtgttcctgcgccggttgcattcgattcctgtttgt
aattgtccttttaacagcgatcgcgtatttcgtctcgctcaggcgcaatc
acgaatgaataacggtttggttgatgcgagtgattttgatgacgagcgta
atggctggcctgttgaacaagtctggaaagaaatgcataagcttttgcca
ttctcaccggattcagtcgtcactcatggtgatttctcacttgataacct
tattttgacgaggggaaattaataggttgtattgatgttggacgagtcg
gaatcgcagaccgataccaggatcttgccatcctatggaactgcctcggt
gagttttctccttcattacagaaacggctttttcaaaaatatggtattga
taatcctgatatgaataaattgcagtttcatttgatgctcgatgagtttt
tctaaccctgatcactgtggaatgtgtgtcagttagggtgtggaaagtcc
ccaggctccccagcaggcagaagtatgcaaagcatgcatctcaattagtc
agcaaccaggtgtggaaagtccccaggctccccagcaggcagaagtatgc
aaagcatgcatctcaattagtcagcaaccatagtcccgcccctaactccg
cccatcccgcccctaactccgcccaggatccgctctagatggccattgca
tacgttgtatccatatcataatatgtacatttatattggctcatgtccaa
cattaccgccatgttgacattgattattgactagttattaatagtaatca
attacggggtcattagttcatagcccatatatggagttccgcgttacata
acttacggtaaatggcccgcctggctgaccgcccaacgacccccgcccat
tgacgtcaataatgacgtatgttcccatagtaacgccaatagggactttc
cattgacgtcaatgggtggagtatttacggtaaactgcccacttggcagt
acatcaagtgtatcatatgccaagtacgccccctattgacgtcaatgacg
gtaaatggcccgcctggcattatgcccagtacatgaccttatgggacttt
cctacttggcagtacatctacgtattagtcatcgctattaccatggtgat
gcggttttggcagtacatcaatgggcgtggatagcggtttgactcacggg
gatttccaagtctccaccccattgacgtcaatgggagtttgttttggcac
caaaatcaacgggactttccaaaatgtcgtaacaactccgccccattgac
gcaaatgggcggtaggcgtgtacggtgggaggtctatataagcagagctc
gtttagtgaaccgtcagatcgcctggagacgccatccacgctgttttgac
ctccatagaagacaccgggaccgatccagcctccgcggctcgcatctctc
cttcacgcgcccgccgccctacctgaggccgccatccacgccggttgagt
cgcgttctgccgcctcccgcctgtggtgcctcctgaactgcgtccgccgt
ctaggtaagtttaaagctcaggtcgagaccgggcctttgtccggcgctcc -continued

```
cttggagcctacctagactcagccggctctccacgctttgcctgaccctg cttgctcaactctagttctctcgttaacttaatgagacagatagaaactg gtcttgtagaaacagagtagtcgcctgcttttctgccaggtgctgacttc tctcccctgggcttttttcttttctcaggttgaaaagaagaagacgaag aagacgaagaagacaaagccgccaccatggatgcaatgaagagagggctc tgctgtgtgctgctgctgtgtggagcagtcttcgtttcgcccagcggtac cggatccgtcgacggggggagatcttttcctctgccaaaaattatggg
```

-continued

```
gacatcatgaagccccttgagcatctgacttctggctaataaaggaaatt tattttcattgcaatagtgtgttggaattttttgtgtctctcactcggaa ggacataagggcggccgctagc
```

SEQ ID NO: 14: NTC8482, NTC8682, NTC7482, NTC7682 optimized TPA-SalI secretion signal (87 bp)

```
atggatgcaatgaagagagggctctgctgtgtgctgctgctgtgtggagc agtcttcgtttcgcccagcggtaccggatccgtcgac
```

---

What is claimed is:

1. A PAS-BH region pUC origin plasmid vector composition, comprising:
   a PAS-BH region comprising at least 90% sequence identity to the sequence set forth as SEQ ID NO: 4, and
   a pUC origin plasmid vector wherein said PAS-BH region is operably linked to said pUC origin and wherein said PAS-BH region pUC origin plasmid vector does not comprise the repressor of primer (ROP) gene and wherein plasmid copy number of said PAS-BH region pUC origin plasmid vector is increased in shake flask or fermentation culture of transformed bacterial cells compared to said pUC origin plasmid vector.

2. The PAS-BH region pUC origin plasmid vector composition of claim 1, wherein the vector comprises a sequence selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

* * * * *